United States Patent
Wu et al.

(10) Patent No.: US 11,952,355 B2
(45) Date of Patent: Apr. 9, 2024

(54) METHOD OF PREPARING MALONONITRILE OXIME ETHER COMPOUND AND INTERMEDIATE COMPOUND

(71) Applicant: Shenyang Sinochem Agrochemicals R&D Co., Ltd., Liaoning (CN)

(72) Inventors: Hongfei Wu, Liaoning (CN); Xueming Cheng, Liaoning (CN); Libao Xu, Liaoning (CN); Chunxiao Guo, Liaoning (CN); Jingbo Xu, Liaoning (CN); Ningning Sun, Liaoning (CN); Haibo Yu, Liaoning (CN)

(73) Assignee: Shenyang Sinochem Agrochemicals R&D Co., Ltd., Liaoning (CN)

( * ) Notice: Subject to any disclaimer, the term of this patent is extended or adjusted under 35 U.S.C. 154(b) by 238 days.

(21) Appl. No.: 17/259,565

(22) PCT Filed: Jun. 17, 2019

(86) PCT No.: PCT/CN2019/091540
§ 371 (c)(1),
(2) Date: Jan. 12, 2021

(87) PCT Pub. No.: WO2020/010988
PCT Pub. Date: Jan. 16, 2020

(65) Prior Publication Data
US 2022/0055996 A1 Feb. 24, 2022

(30) Foreign Application Priority Data
Jul. 13, 2018 (CN) .......................... 201810771581.7

(51) Int. Cl.
| | | |
|---|---|---|
| C07D 277/24 | (2006.01) | |
| C07C 253/20 | (2006.01) | |
| C07C 253/30 | (2006.01) | |
| C07C 255/64 | (2006.01) | |
| C07D 213/61 | (2006.01) | |
| C07D 215/14 | (2006.01) | |

(52) U.S. Cl.
CPC .......... *C07D 277/24* (2013.01); *C07C 253/20* (2013.01); *C07C 253/30* (2013.01); *C07C 255/64* (2013.01); *C07D 213/61* (2013.01); *C07D 215/14* (2013.01)

(58) Field of Classification Search
CPC .. C07D 277/24; C07D 231/61; C07D 215/14; C07C 253/20; C07C 253/30; C07C 255/64
See application file for complete search history.

(56) References Cited

U.S. PATENT DOCUMENTS

| | | | | |
|---|---|---|---|---|
| 3,919,284 | A | * | 11/1975 | Lin ...................... C07F 9/1657 987/211 |
| 3,954,992 | A | | 5/1976 | Davidson |
| 4,178,383 | A | | 12/1979 | Brandes et al. |

FOREIGN PATENT DOCUMENTS

| | | |
|---|---|---|
| CN | 104177408 A | 12/2014 |
| CN | 105330612 A | 2/2016 |
| CN | 105377812 A | 3/2016 |
| CN | 106916084 A | 7/2017 |
| DE | 2657145 A1 | 6/1978 |
| EP | 0051784 A1 | 5/1982 |
| EP | 0097280 A2 | 1/1984 |
| EP | 3395795 A1 | 10/2018 |
| GB | 2094794 A | 9/1982 |
| WO | 2017107939 A1 | 6/2017 |

OTHER PUBLICATIONS

Burugupalli, S. et al. "Investigation of Benzoyloximes as Benzoylating Reagents: Benzoyl-Oxyma as a Selective Benzoylating Reagent" Organic & Biomolecular Chemistry, vol. vol. 14, Oct. 29, 29, 2015 (Oct. 29, 2015), pp. 97-104.

(Continued)

*Primary Examiner* — Samantha L Shterengarts
*Assistant Examiner* — Karen Cheng
(74) *Attorney, Agent, or Firm* — Samson G. Yu

(57) ABSTRACT

Provided are a method of preparing a malononitrile oxime ether compound and an intermediate compound. The malononitrile oxime ether compound has a structure as shown in formula (VII), wherein W is selected from aryl or heteroaryl. The preparation method comprises: reacting a first raw material with a second raw material in the presence of a first solvent and a catalyst to obtain the intermediate compound, wherein the first raw material has a structure as shown in formula (IV), and the second raw material has a structure as shown in formula (V); and subjecting the intermediate compound, and a dehydrant to a dehydration reaction in the present of a second solvent to obtain the malononitrile oxime ether compound. Furthermore, the malononitrile oxime ether compound is obtained through one-step dehydration reaction. using the preparation method, is advantageous for improving the yield of malononitrile oxime ethers and reducing the cost.

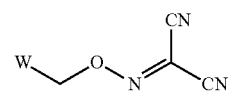

Formula (VII)

16 Claims, No Drawings

(56) References Cited

OTHER PUBLICATIONS

The extended European search report of the corresponding EP patent application No. 19835086.0, dated Mar. 14, 2022.
Gewald K et al: "4-Aminoisoxazole Surch Thorpe-Cyclisierung// 4-Aminoisoxazoles by Thorpe Cyclization", Liebigs Annalen Der Chemie, Cerlag Chemie GmbH. Weinheim, DE, No. 10, Jan. 1, 1980(Jan. 1, 1980), pp. 1623-1629, XP 009031092, ISSN:0170-2041.
Kanai T et al: "Efficient preparation of (z)-2-(5-amino-1,2,4-thiadiazol-3-yl)-2-[(fluorometaoxy) imino] acetic acid", Bulletin of the Chemical Society of Japan, Chemical Society of Hapan, Nippon Kagakukai, JP, vol. 66, No. 8, a Jan. 1993(Jan. 1, 1993), pp. 2335-2338, XP002408735, ISSN: 0009-2673, DOI:10.1246/BCSJ.66.2335.
STN (RN1379432-57-1, RN89721-60-8, RN89721-55-1, RN82804-93-1, RN82804-82-8).

\* cited by examiner

METHOD OF PREPARING MALONONITRILE OXIME ETHER COMPOUND AND INTERMEDIATE COMPOUND

TECHNICAL FIELD

The prevent disclosure relates to the field of organic synthesis, in particular to a method of preparing a malononitrile oxime ether compound and an intermediate compound.

BACKGROUND

The existing literatures provide a synthetic method for the malononitrile oxime ether compound with good control effect on bacterial diseases and fungal diseases in plants, as shown in following formulas:

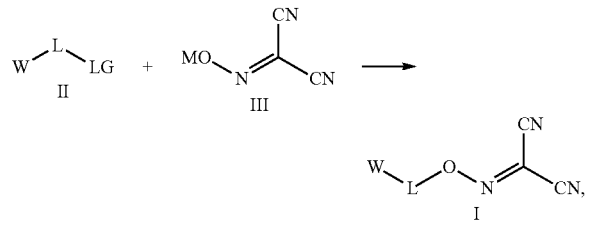

wherein LG represents leaving groups, selected from halogen or other conventional nucleofugal groups, for example, trifluoromethyl groups, mesyloxy groups, tosyloxy groups or the like; M represents a cation, for example, Na$^+$, K$^+$, C$_S^+$, Ag$^+$, NH$_4^+$ or the like; W represents various aryl groups or heteroaryl groups; and L represents various chain bridges.

However, when the malononitrile oxime ether compound represented by formula I is prepared by an existing method, the yield is generally lower than 60%, malononitrile, as a raw material for preparing a compound represented by formula III, is relatively high in cost, and thus the cost of the compound represented by formula III is also relatively high. Therefore, how to develop a synthetic method more suitable for industrial production is an urgent problem in the art.

SUMMARY

A primary objective of the present disclosure is to provide a method of preparing a malononitrile oxime ether compound and an intermediate compound so as to solve the problems of low product yield and high cost when the malononitrile oxime ether compound is prepared by the existing method.

In order to implement the objective, one aspect of the present disclosure provides a preparation method for the malononitrile oxime ether compound. The malononitrile oxime ether compound has a structure represented by a formula (VII),

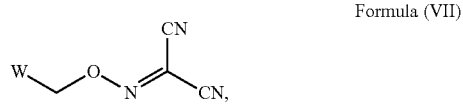

Formula (VII)

wherein W is selected from aryl groups or heteroaryl groups.

The preparation method comprises the following steps: enabling a first raw material to be reacted with a second raw material in the presence of a first solvent and a catalyst to obtain the intermediate compound, the first raw material has a structure represented by a formula (IV), the second raw material has a structure represented by a formula (V), and a synthetic route being as follows:

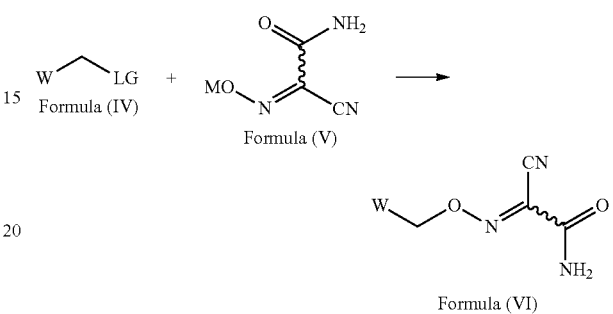

wherein LG represents leaving groups, M is selected from monovalent cations, W is selected from aryl groups or heteroaryl groups, "〰" represents a chemical bond, and a configuration of double bonds may be (Z)- or (E)-; and performing dehydration reaction with the intermediate compound represented by the formula (VI) and a dehydrating agent in the presence of a second solvent to obtain the malononitrile oxime ether compound, a synthetic route being as follows:

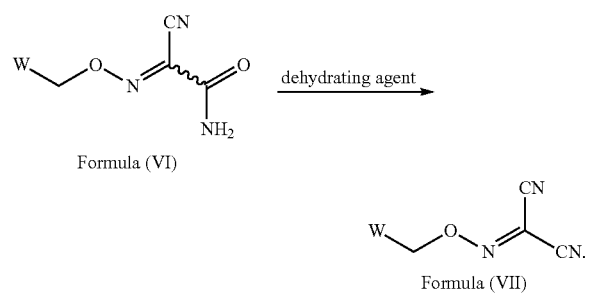

In order to achieve the objective, another aspect of the present disclosure provides an intermediate compound. The intermediate compound has a structure represented by a formula (VI):

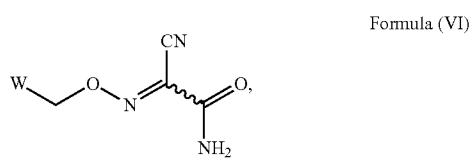

wherein W is selected from aryl groups or heteroaryl groups, "〰" represents a chemical bond, and a configuration of double bonds may be (Z)- or (E)-.

By applying a technical solution of the present disclosure, in the preparation method, the second raw material represented by the formula (V) is prepared with cheap and available cyanoacetamide as a raw material; then the intermediate compound represented by the formula (VI) is prepared by the first raw material represented by the formula (IV) and the second raw material represented by the formula (V) in the presence of the catalyst and the first solvent; and then dehydration is performed on the intermediate compound represented by the formula (VI) in the presence of the second solvent and a dehydrating agent to obtain the required malononitrile oxime ether compound. A preparation process of an intermediate takes relatively cheap cyanoacetamide as a raw material, the whole process is moderate in reaction condition, the yield of the intermediate compound is high, and cost is low; the dehydration process of the intermediate compound is simple without special treatment, and the required malononitrile oxime ether compound may be obtained with one-step dehydration reaction only; and therefore, by the preparation method, the yield of malononitrile oxime ethers is increased and the cost is reduced.

DETAILED DESCRIPTION OF THE EMBODIMENTS

It should be noted that the examples of the present application and the characteristics in the examples can be combined with other another without conflict. The present disclosure will be explained in details with combination with the examples below.

As described in the background of the present disclosure, the problems of low yield of a product and high preparation cost exist when the malononitrile oxime ether compound is prepared by the existing method. In order to solve the technical problems, the present disclosure provides a preparation method for the malononitrile oxime ether compound. The malononitrile oxime ether compound has a structure represented by a formula (VII),

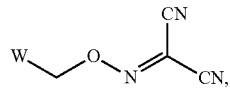

Formula (VII)

wherein W is selected from aryl groups or heteroaryl groups.

The preparation method comprises the following steps: enabling the first raw material to be reacted with the second raw material in the presence of the first solvent and the catalyst to obtain the intermediate compound, the first raw material has a structure represented by a formula (IV), the second raw material has a structure represented by a formula (V), and a synthetic route being as follows:

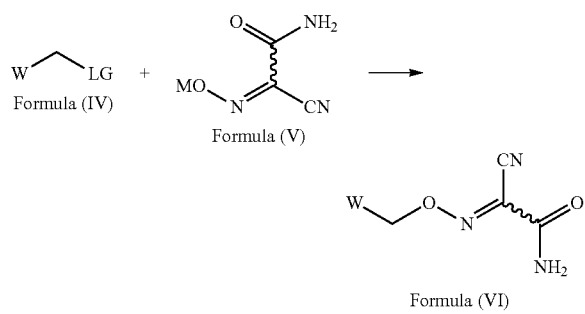

Formula (IV)
Formula (V)
Formula (VI)

wherein LG represents leaving groups, M is selected from monovalent cations, W is selected from aryl groups or heteroaryl groups, " " represents a chemical bond, and a configuration of double bonds may be (Z)- or (E)-; and performing dehydration reaction with the intermediate compound represented by the formula (VI) and a dehydrating agent in the presence of a second solvent to obtain the malononitrile oxime ether compound, wherein a synthetic route being as follows:

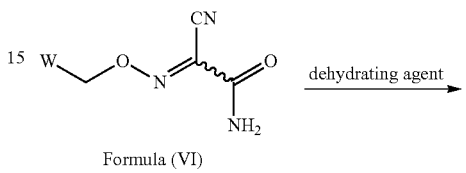

Formula (VI)

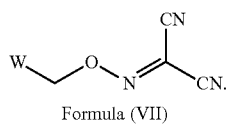

Formula (VII)

In the preparation method, the second raw material represented by the formula (V) is prepared with cheap and available cyanoacetamide as a raw material; then the intermediate compound represented by the formula (VI) is prepared by the first raw material represented by the formula (IV) and the second raw material represented by the formula (V) in the presence of the catalyst and the first solvent; and then dehydration is performed on the intermediate compound represented by the formula (VI) in the presence of the second solvent and a dehydrating agent to obtain the required malononitrile oxime ether compound. A preparation process of an intermediate takes relatively cheap cyanoacetamide as a raw material, the whole process is moderate in reaction condition, the yield of the intermediate compound is high, and the cost is low; the dehydration process of the intermediate compound is simple without special treatment, and the required malononitrile oxime ether compound may be obtained with one-step dehydration reaction only; and therefore, by the preparation method, the yield of malononitrile oxime ethers is increased and the cost is much lower.

The malononitrile oxime ether compound is a compound with good control effect on bacterial diseases and fungal diseases of plants, and therefore, the preparation method provides a novel and effective way of industrial development for the malononitrile oxime ether compound.

In a preferred embodiment, W is selected from aryl groups or heteroaryl groups rather than unsubstituted phenyl groups; and in order to further improve the dehydration performance of the intermediate compound and reduce the synthesis difficulty, a substituent in the structure represented by the formula (VI) is preferably selected. In a preferred embodiment, W is selected from, but not limited to, any one of $W^1$-$W^{84}$. See Table 1 for the structure.

TABLE 1
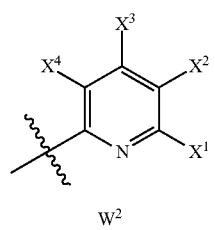
W¹
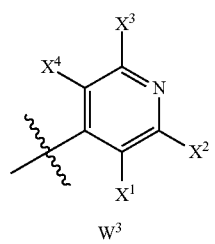
W²
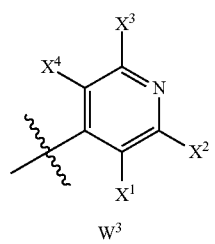
W³
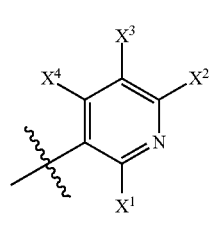
W⁴
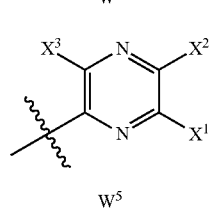
W⁵
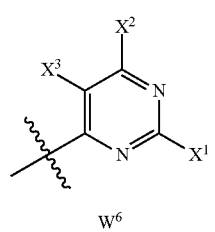
W⁶
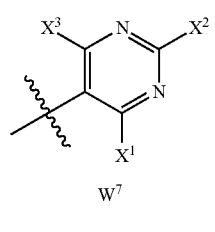
W⁷
TABLE 1-continued
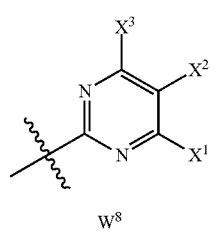
W⁸
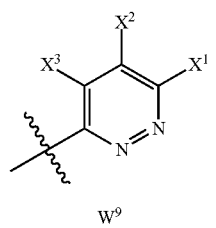
W⁹
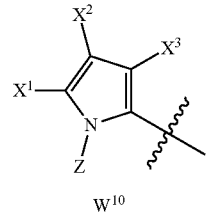
W¹⁰
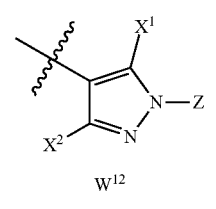
W¹¹
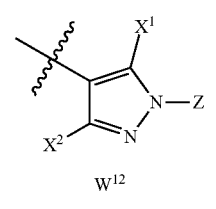
W¹²
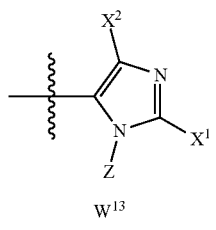
W¹³
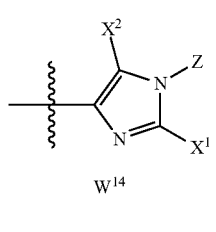
W¹⁴

TABLE 1-continued
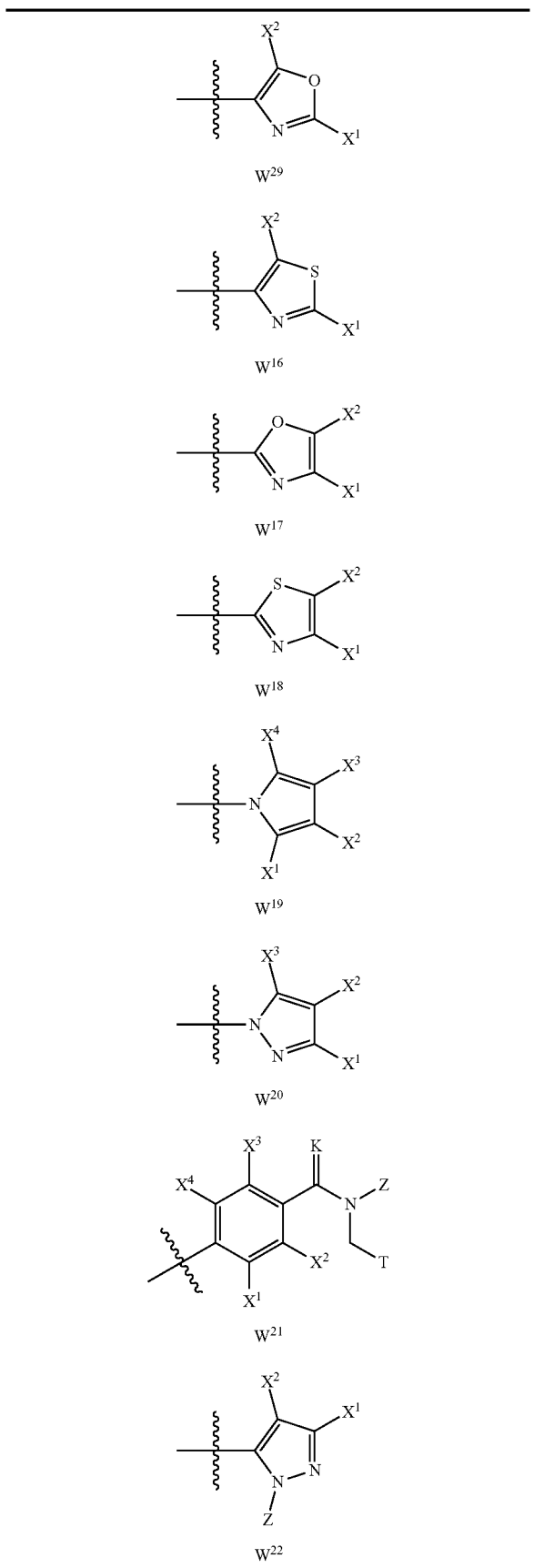
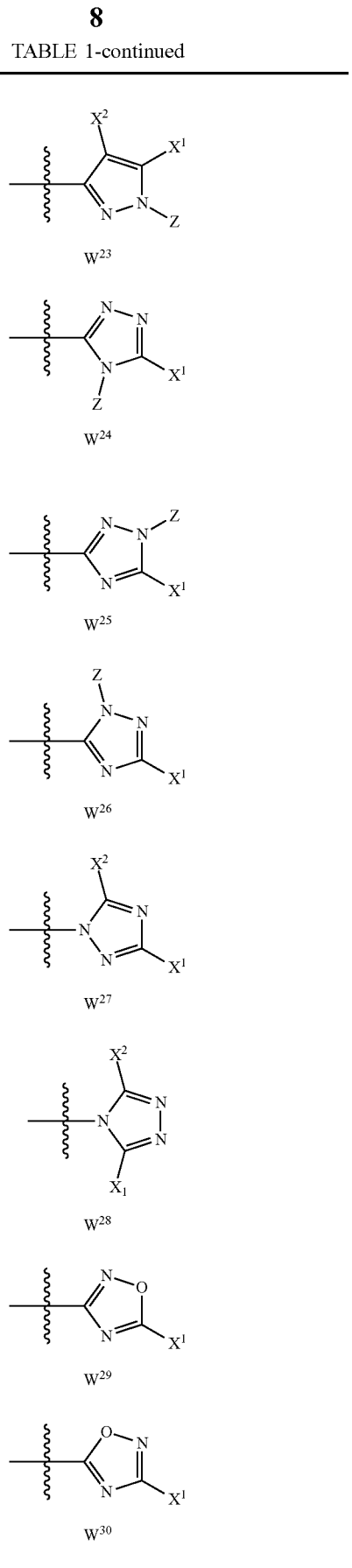

TABLE 1-continued
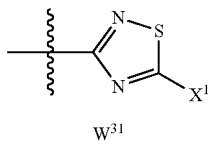
W31
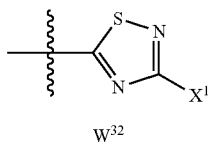
W32
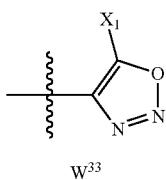
W33
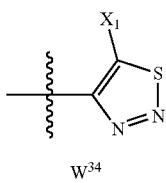
W34
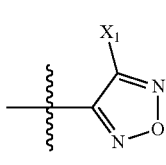
W35
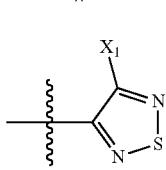
W36
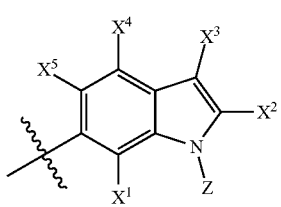
W37
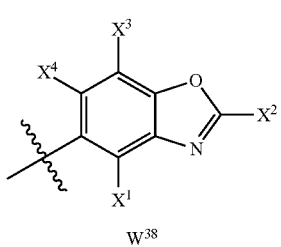
W38
TABLE 1-continued
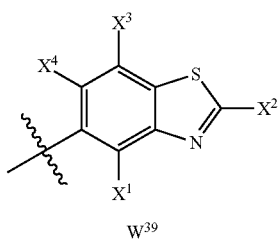
W39
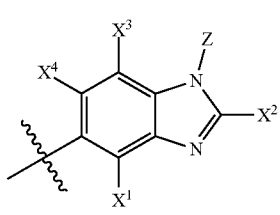
W40
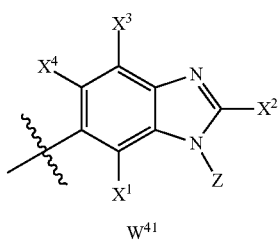
W41
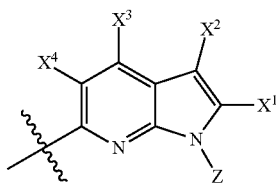
W42
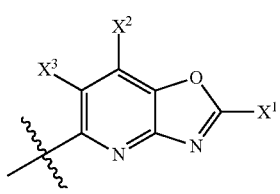
W43
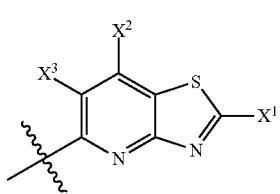
W44

TABLE 1-continued
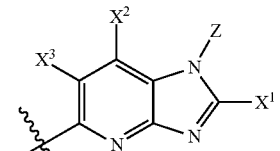
W⁴⁵
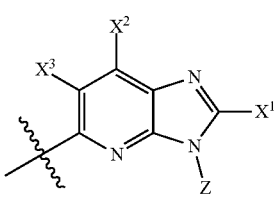
W⁴⁶
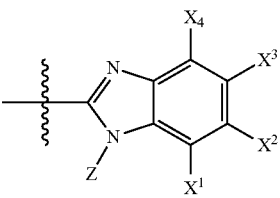
W⁴⁷
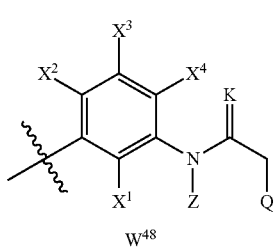
W⁴⁸
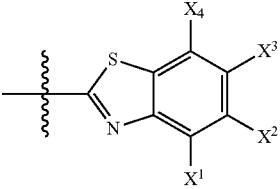
W⁴⁹
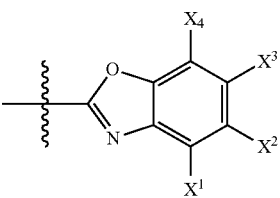
W⁵⁰
TABLE 1-continued
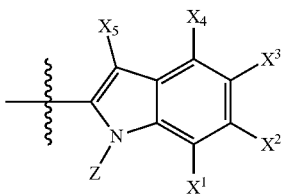
W⁵¹
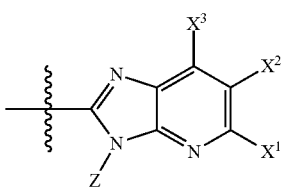
W⁵²
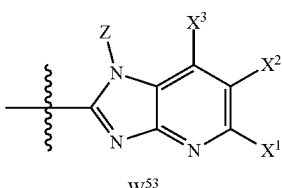
W⁵³
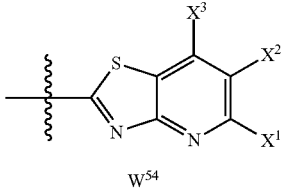
W⁵⁴
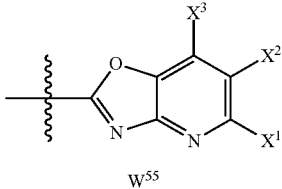
W⁵⁵
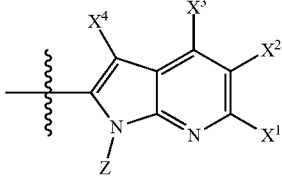
W⁵⁶
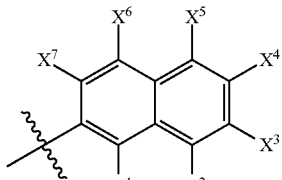
W⁵⁷

TABLE 1-continued
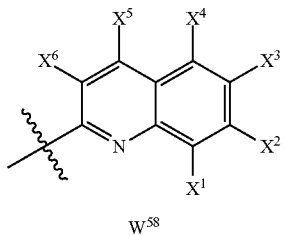
W⁵⁸
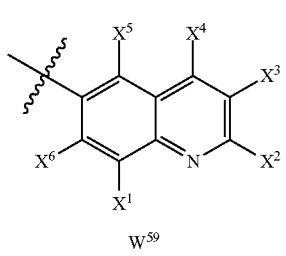
W⁵⁹
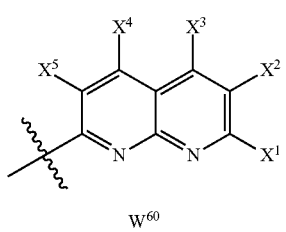
W⁶⁰
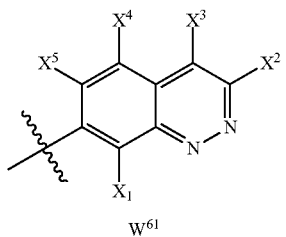
W⁶¹
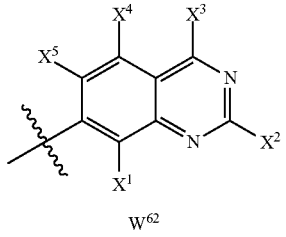
W⁶²
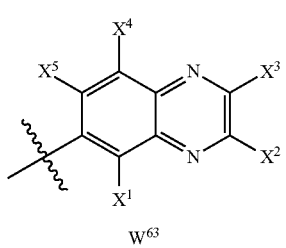
W⁶³
TABLE 1-continued
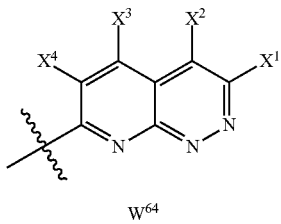
W⁶⁴
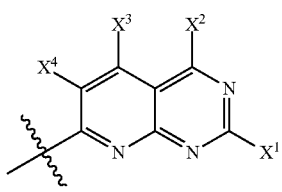
W⁶⁵
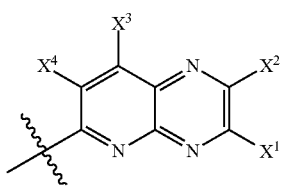
W⁶⁶
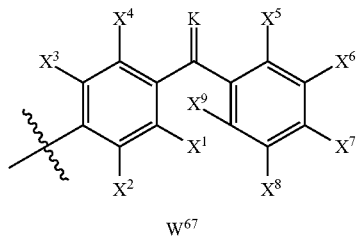
W⁶⁷
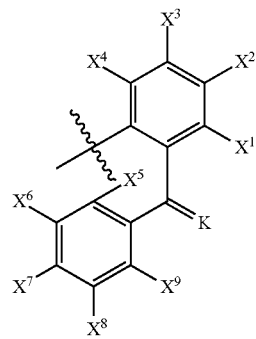
W⁶⁸
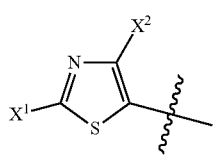
W⁶⁹

TABLE 1-continued
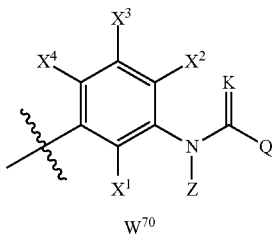
W⁷⁰
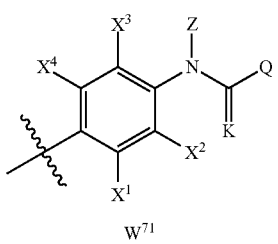
W⁷¹
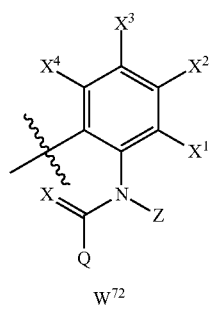
W⁷²
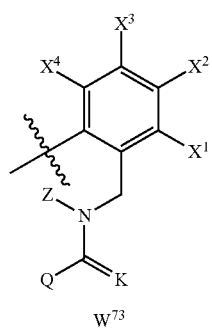
W⁷³
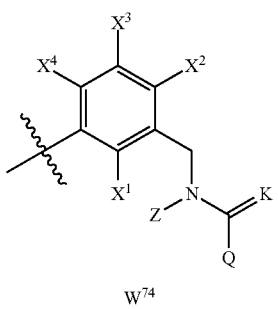
W⁷⁴
TABLE 1-continued
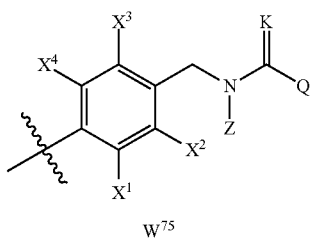
W⁷⁵
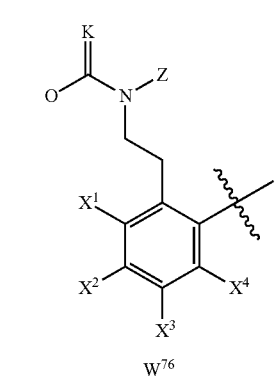
W⁷⁶
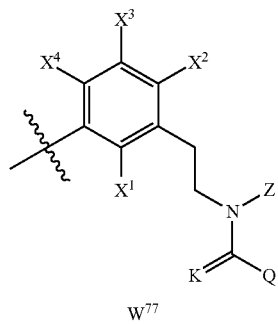
W⁷⁷
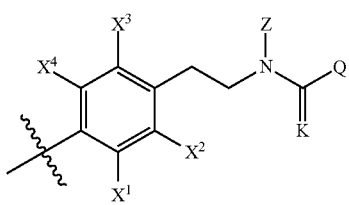
W⁷⁸
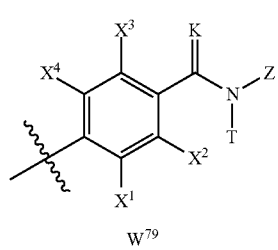
W⁷⁹

TABLE 1-continued

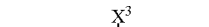

W80

W81

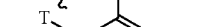

W82

W83

W84

Wherein $X^1$, $X^2$, $X^3$, $X^4$, $X^5$, $X^6$, $X^7$, $X^8$ and $X^9$ independently selected from, but not limited to, hydrogen, halogens, cyano groups, nitro groups, —$SF_5$, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, $C_1$-$C_8$ alkoxy groups; $C_1$-$C_8$ alkyl groups, —$OR^3$, —$C(=O)OR^3$, —$N(R^4)S(=O)_2R^5$, —$S(=O)_2NR^3R^5$, —$N(R^4)C(=O)OR^3$, —$CR^4=NOR^3$, —$CH_2ON=C(CN)_2$, —$C(=O)SR^3$, —$C(=S)OR^3$, —$C(=S)SR^3$, —$CR^4=NR^5$, —$CR^4=N—NR^3R^5$, —$OSiR^4R^5R^6$, —$OC(=O)R^4$, —$OC(=O)OR^3$, —$OC(=O)NR^3R^4$, —$OC(=S)NR^3R^4$, —$NR^3R^4$, —$N(R^4)C(=O)NR^3R^5$, —$N(R^4)C(=S)NR^3R^5$, —$N=CR^4R^5$, —$N=C—NR^3R^4$, —$N(R^4)C(=NR^5)NR^3R^6$, —$N(R^4)OR^3$, —$N(R^4)NR^3R^5$, —$N=NR^4$, —$N(R^4)S(=O)R^5$, —$N(R^4)S(=O)_2OR^3$, —$N(R^4)S(=O)OR^3$, —$N(R^4)S(=O)NR^3R^5$, —$N(R^4)S(=O)_2NR^3R^5$, $NR^4C(=O)R^5$, —$SR^3$, —$S(=O)_2R^4$, —$S(=O)R^4$, —$S(=O)OR^3$, —$S(=O)NR^3R^4$, —$S(=O)_2OR^3$, —$S(=O)NR^3R^4$, —$SiR^3R^4R^5$, a group $G^1$ or a group $G^1$ optionally substituted with a substitutent $J^1$, wherein the group $G^1$ is selected from, but not limited to, phenyl groups, pyridyl groups, pyrazolyl groups, thiazolyl groups, isothiazolyl groups or thiadiazolyl groups, and the substitutent $J^1$ is selected from, but not limited to, the halogens, cyano groups, the nitro groups, $C_1$-$C_8$ alkyl groups, the haloalkyl groups of $C_1$-$C_8$, alkoxy groups of $C_1$-$C_8$, haloalkoxy groups of $C_1$-$C_8$, alkylthio groups of $C_1$-$C_8$ or haloalkylthio groups of $C_1$-$C_8$;

Z is selected from, but not limited to, hydrogen, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, aryl groups, $C_1$-$C_8$ alkyl groups substituted with $C_1$-$C_8$ aryl groups, $C_1$-$C_8$ alkyl groups substituted with $C_1$-$C_8$ alkoxy groups, —$C(=O)R^3$ or —$C(=O)OR^3$;

K is selected from, but not limited to, oxygen, sulfur, $NR^3$, N—$OR^4$ or N—$NR^3R^4$;

$R^3$ is selected from, but not limited to, hydrogen, $C_1$-$C_8$ alkyl groups, $C_1$-$C_8$ haloalkyl groups, $C_3$-$C_6$ cycloalkyl groups, $C_1$-$C_8$ alkoxycarbonyl groups, $C_2$-$C_8$ alkenyl groups, $C_2$-$C_8$ haloalkenyl groups, $C_2$-$C_8$ alkynyl groups, $C_2$-$C_8$ haloalkynyl groups, a group $G^2$ or a group $G^2$ optionally substituted with a substitutent $J^2$, wherein the group $G^2$ is selected from phenyl groups, pyridyl groups, pyrazolyl groups, thiazolyl groups, isothiazolyl groups or thiadiazolyl groups, and the substitutent $J^2$ is selected from halogens, cyano groups, nitro groups, hydroxyl groups, thiol groups, amino groups, —$CONH_2$, —$COOH$, —$CHO$, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, amino groups substituted with $C_1$-$C_3$ alkyl, amino groups substituted with $C_1$-$C_3$ dialkyl, amino groups substituted with $C_3$-$C_6$ cycloalkyl, $C_1$-$C_3$ alkoxycarbonyl groups, $C_1$-$C_3$ alkylsulphonyl groups, aminocarbonyl groups substituted with $C_1$-$C_3$ alkyl or sulfonamide groups substituted with $C_1$-$C_3$ alkyl;

$R^4$, $R^5$ and $R^6$ independently include, but not limited to, hydrogen, $C_1$-$C_8$ alkyl groups, $C_1$-$C_8$ haloalkyl groups, $C_3$-$C_6$ cycloalkyl groups, $C_1$-$C_8$ alkoxy groups, $C_1$-$C_8$ haloalkoxy groups, $C_1$-$C_8$ alkoxycarbonyl groups, $C_2$-$C_8$ alkenyl groups, $C_2$-$C_8$ haloalkenyl groups, $C_2$-$C_8$ alkynyl groups, $C_2$-$C_8$ haloalkynyl groups, a group $G^3$ or a group $G^3$ optionally substituted with a substitutent $J^3$, wherein the group $G^3$ is selected from phenyl groups, pyridyl groups, pyrazolyl groups, thiazolyl groups, isothiazolyl groups or thiadiazolyl groups, and the substitutent $J^3$ is selected from halogens, cyano groups, nitro groups, hydroxyl groups, thiol groups, amino groups, —$CONH_2$, —$COOH$, —$CHO$, $C_1$-$C_4$ alkyl groups, $C_1$-$C_4$ haloalkyl groups, $C_3$-$C_6$ cycloalkyl groups, C₁-C₃ alkoxy groups, C₁-C₃ haloalkoxy groups, C₁-C₃ alkylthio groups, C₁-C₃ haloalkylthio groups, C₁-C₃ alkylamino groups, C₁-C₃ dialkylamino groups, C₃-C₆ cycloalkylamino groups, C₁-C₃ alkoxycarbonyl groups, C₁-C₃ alkylsulphonyl groups, C₁-C₃ alkylaminocarbonyl groups or C₁-C₃ alkylaminosulfonyl groups;

Q is selected from, but not limited to, a group G⁴ or a group G⁴ optionally substituted with a substitutent J⁴, the group G⁴ is selected from phenyl groups, pyridyl groups, pyrazolyl groups, thiazolyl groups, isothiazolyl groups or thiadiazolyl groups, and the substitutent J⁴ is selected from halogens, cyano groups, nitro groups, hydroxyl groups, thiol groups, amino groups, —CONH₂, —COOH, —CHO, C₁-C₄ alkyl groups, C₁-C₄ haloalkyl groups, C₃-C₆ cycloalkyl groups, C₁-C₃ alkoxy groups, C₁-C₃ haloalkoxy groups, C₁-C₃ alkylthio groups, C₁-C₃ haloalkylthio groups, C₁-C₃ alkylamino groups, C₁-C₃ dialkylamino groups, C₃-C₆ cycloalkylamino groups, C₁-C₃ alkoxycarbonyl groups, C₁-C₃ alkylsulphonyl groups, C₁-C₃ alkylaminocarbonyl groups or C₁-C₃ alkylaminosulfonyl groups; and T is selected from, but not limited to, cyano groups, C₁-C₈ alkyl groups, C₁-C₈ haloalkyl groups, C₃-C₆ cycloalkyl groups, C₂-C₈ alkenyl groups, C₂-C₈ haloalkenyl groups, C₂-C₈ alkynyl groups, C₂-C₈ haloalkynyl groups, a group G⁵ or a group G⁵ optionally substituted with a substitutent J⁵, wherein the group G⁵ is selected from phenyl groups, pyridyl groups, pyrazolyl groups, thiazolyl groups, isothiazolyl groups or thiadiazolyl groups, and the substitutent J⁵ is selected from halogens, cyano groups, nitro groups, hydroxyl groups, thiol groups, amino groups, —CONH₂, —COOH, —CHO, C₁-C₄ alkyl groups, C₁-C₄ haloalkyl groups, C₃-C₆ cycloalkyl groups, C₁-C₃ alkoxy groups, C₁-C₃ haloalkoxy groups, C₁-C₃ alkylthio groups, C₁-C₃ haloalkylthio groups, C₁-C₃ alkylamino groups, C₁-C₃ dialkylamino groups, C₃-C₆ cycloalkylamino groups, C₁-C₃ alkoxycarbonyl groups, C₁-C₃ alkylsulphonyl groups, C₁-C₃ alkylaminocarbonyl groups or C₁-C₃ alkylaminosulfonyl groups, but the W is not selected from the unsubstituted phenyl groups.

In a preferred embodiment, the W is selected from, but not limited to W¹, W², W³, W⁴, W¹², W¹⁶, W¹⁸, W²¹, W⁴⁸, W⁵⁸, W⁵⁹, W⁶⁷, W⁶⁸, W⁶⁹, W⁷⁰, W⁷¹, W⁷², W⁷⁴, W⁷⁹, W⁸⁰, W⁶¹, W⁶² or W⁶³;

X¹, X², X³, X⁴, X⁵, X⁶, X⁷, X⁸ and X⁹ independently include, but not limited to, hydrogen, fluorine, chlorine, bromine, cyano groups, nitro groups, methyl groups, ethyl groups, isopropyl groups, chloromethyl groups, bromomethyl groups, difluoromethyl groups, trifluoromethyl groups, heptafluoroisopropyl groups, —OR³, —C(=O)OR³, —N(R⁴)S(=O)₂R⁵, —S(=O)₂NR³R⁴, —N(R⁴)C(=O)OR³, —CR⁴=NOR³, —CH₂ON=C(CN)₂, NR⁴C(=O)R⁵, the group G¹ or the group G¹ optionally substituted with a substitutent J¹, wherein the group G¹ is selected from phenyl groups or pyridyl groups, and the substitutent J¹ is selected from halogens, cyano groups, nitro groups, trifluoromethyl groups, heptafluoropropyl groups, heptafluoroisopropyl groups, methoxy groups or trifluoromethoxy groups;

Z is selected from, but not limited to, hydrogen, methyl groups or benzyl groups;

K is oxygen;

R³ is selected from, but not limited to, hydrogen, methyl groups, ethyl groups, propyl groups, isopropyl groups, cyclopropyl groups, difluoromethyl groups, trifluoromethyl groups, heptafluoropropyl groups, heptafluoroisopropyl groups, methoxycarbonyl groups, the group G² or the group G² optionally substituted with the substitutent J², wherein the group G² is selected from phenyl groups and pyridyl groups, and the substitutent J² is selected from halogens, cyano groups, nitro groups or trifluoromethyl groups;

R⁴ and R⁵ independently include, but not limited to, hydrogen, methyl groups, ethyl groups, propyl groups, isopropyl groups, cyclopropyl groups, difluoromethyl groups, trifluoromethyl groups, heptafluoropropyl groups, heptafluoroisopropyl groups, methoxy groups, trifluoromethoxy groups, methoxycarbonyl groups, the group G³ or the group G³ optionally substituted with the substitutent J³, wherein the group G³ is selected from phenyl groups and pyridyl groups, and the substitutent J³ is selected from halogens, cyano groups, nitro groups, methyl groups, ethyl groups, propyl groups, chloromethyl groups, bromomethyl groups, trifluoromethyl groups, heptafluoroisopropyl groups, methoxy groups or trifluoromethoxy groups;

Q is selected from, but not limited to, Q¹, Q², Q³, Q⁴, Q⁵, Q⁶, Q⁷, Q⁸, Q⁹ and Q¹⁰, phenyl groups, pyridyl groups or the group G⁴ optionally substituted with the substitutent J⁴, wherein the group G⁴ is selected from phenyl groups or pyridyl groups, and the substitutent J⁴ is selected from halogens, cyano groups, nitro groups, hydroxyl groups, thiol groups, amino groups, chloromethyl groups, bromomethyl groups, difluoromethyl groups, trifluoromethyl groups, heptafluoroisopropyl groups, methoxy groups, ethoxy groups, propoxy groups, isopropoxy groups, trifluoromethoxy groups, methylthio groups, ethylthio groups, trifluoromethylthio groups and trifluoroethylthio groups, wherein structures of Q¹-Q¹⁰ are in Table 2.

TABLE 2

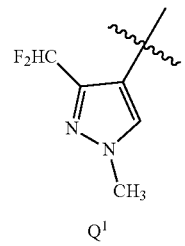

Q¹

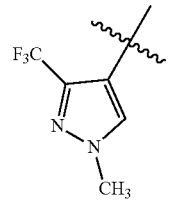

Q²

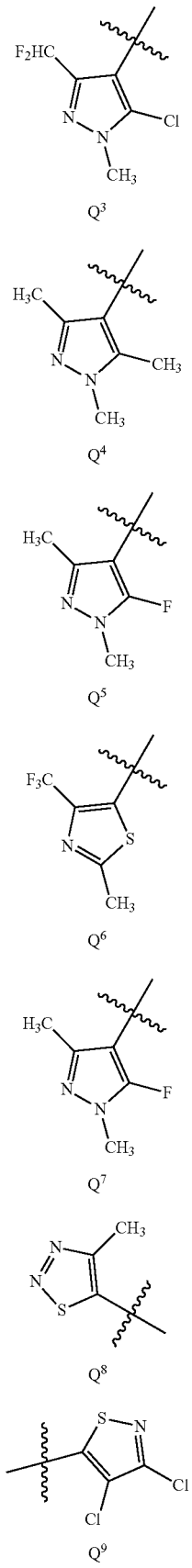
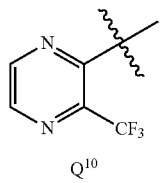

T is selected from, but not limited to, cyano groups, methyl groups, ethyl groups, propyl groups, isopropyl groups, cyclopropyl groups, trifluoroethyl groups, difluoroethyl groups, cyclopropyl groups, cyclobutyl groups, cyclopentyl groups, cyclohexyl groups, the group $G^5$ or the group $G^5$ optionally substituted with the substitutent $J^5$, wherein the group $G^5$ is selected from phenyl groups and pyridyl groups, and the substitutent $J^5$ is selected from halogens, cyano groups, nitro groups, methyl groups, ethyl groups, propyl groups, isopropyl groups, chloromethyl groups, bromomethyl groups, trifluoromethyl groups, heptafluoroisopropyl groups, cyclopropyl groups, cyclobutyl groups, cyclopentyl groups, cyclohexyl groups, methoxy groups, ethoxy groups, propoxy groups, isopropoxy groups, trifluoromethoxy groups, methylthio groups, ethylthio groups, trifluoromethylthio groups or trifluoroethylthio groups.

Further preferably, W is selected from, but not limited to, $W^1$, $W^2$, $W^3$, $W^4$, $W^{16}$, $W^{18}$, $W^{59}$ or $W^{69}$.

In a preferred embodiment, in the dehydration reaction process, a molar ratio of the intermediate compound to the dehydrating agent is 1 to (1-20). The molar ratio of the intermediate compound to the dehydrating agent is selected from, but not limited to, the above range. However, further improvement in dehydration efficiency of the intermediate compound represented by the formula (VI) is facilitated if the molar ratio is limited in the above range.

In a preferred embodiment, the dehydrating agent is selected from, but not limited to, one or more selected from a group consisting of acetic anhydride, bistrichloromethyl carbonate (triphosgene), thionyl chloride, phosphorus oxychloride and phosphorus pentoxide. The type of the dehydrating agent is selected from, but not limited to, the above types. However, further improvement in dehydration efficiency of the intermediate compound represented by the formula (VI) is facilitated if the above types are selected. Preferably, the dehydrating agent is thionyl chloride and/or phosphorus oxychloride.

The second solvent may be an organic solvent commonly used in the art. The second solvent is selected from, but not limited to, one or more selected from a group consisting of halogenated hydrocarbons (preferably, trichloromethane, tetrachloromethane or dichloroethane), aromatic hydrocarbons (preferably, benzene, toluene or chlorobenzene), nitrile compound (preferably, acetonitrile, propionitrile or butyronitrile) and DMF. More preferably, the second solvent is selected from trichloromethane, dichloroethane, acetonitrile, toluene or DMF.

In a preferred embodiment, a reaction temperature of the dehydration reaction is 0-150° C., and a reaction time is 0.5-48 h; and preferably, the reaction temperature is 20-80° C. The reaction temperature and the reaction time of dehydration reaction include, but not limited to, the above ranges, but further increase in yield of the malononitrile oxime ether compound is facilitated if the reaction temperature and the reaction time are limited in the above ranges.

The group M and the group W may be preferably selected in order to further increase the yield of the intermediate compound.

In a preferred embodiment, LG is halogen, and preferably, is Cl or Br.

In a preferred embodiment, the M is selected from, but not limited to, $Na^+$, $K^+$, $C_S^+$, $Ag^+$ or $NH_4^+$, and preferably, $Na^+$ or $K^+$.

In a preferred embodiment, in the preparation process of the intermediate compound, a molar ratio of the first raw material to the second raw material to the catalyst is 1 to (1-5) to (0.05-0.5). The molar ratio of the first raw material to the second raw material to the catalyst is selected from, but not limited to, the above range. However, further increase in yield of the intermediate compound represented is facilitated if the molar ratio is limited in the above range.

In a preferred embodiment, the catalyst is selected from, but not limited to, one or more selected from a group consisting of NaI, KI, tetrabutylammonium bromide and benzyltriethylammoniumchloride. The type of the catalyst is selected from, but not limited to, the above types; however, further increase in reaction rate of the first raw material to the second raw material is facilitated if the above types are employed, and thus shortening of the reaction period is facilitated.

In the preparation method, the first solvent may employ an organic solvent commonly used in the art. The first solvent is selected from, but not limited to, one or more selected from a group consisting of nitrile compounds (preferably, acetonitrile, propionitrile or butyronitrile), ketone compounds (preferably, acetone, butanone, pentanone or hexanone), DMF, DMSO, 1, 3-dimethyl-2-imidazolidinone and N-methyl-2-pyrrolidone; and more preferably, the first solvent is one or more selected from a group consisting of acetonitrile, acetone, butanone, DMF and DMSO.

In a preferred embodiment, a reaction temperature of the preparation process of the intermediate compound is 0-150° C., and a reaction time is 0.5-48 h. The reaction temperature and the reaction time of the preparation process of the intermediate compound include, but not limited to, the above ranges, but further increase in yield of the intermediate compound is facilitated if the reaction temperature and the reaction time are limited in the above ranges. Preferably, the reaction temperature is 20-80° C.

Another aspect of the present application further provides an intermediate compound for preparing the malononitrile oxime ether compound represented by (VII), and the intermediate compound has a structure represented by a formula (VI):

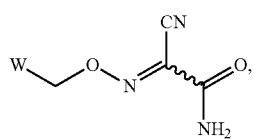

Formula (VI)

wherein the W is selected from, but not limited to aryl groups or heteroaryl groups.

The required malononitrile oxime ether compound may be obtained with the simple dehydration process only by the intermediate compound represented by the formula (VI). The whole process does not need special processing, and the preparation process may be finished with one-step reaction only, such that by preparing the malononitrile oxime ether compound with the intermediate compound, increase in yield of the malononitrile oxime ether compound and reduction in process cost are both facilitated.

Note that, a chemical bond represented by in the formula (VI) means that a configuration of double bonds may be (Z)- or (E)-. Therefore, the intermediate compound may be a compound with a (Z)-configuration, or a compound with an (E)-configuration or a mixture of the two. The chemical bonds, represented by wavy lines, involved in the present application all have the same meaning.

In a preferred embodiment, the W is selected from aryl groups or heteroaryl groups, rather than following groups: the unsubstituted phenyl groups, 4-bromophenyl groups, 4-methoxyphenyl groups, 2-cyanophenyl groups, 3-fluorophenyl groups, 4-nitrophenyl groups, 4-phenylphenyl groups, 4-benzoylphenyl groups, 3-phenoxyphenyl groups and 2-(1, 3-dimethoxy-3-oxo-propenyl-2-yl) phenyl groups or benzo [1, 2, 3] thiadiazole-7-yl groups, wherein structures of 4-bromophenyl groups, 4-methoxyphenyl groups, 2-cyanophenyl groups, 3-fluorophenyl groups, 4-nitrophenyl groups, 4-phenylphenyl groups, 4-benzoylphenyl groups, 3-phenoxyphenyl groups and 2-(1, 3-dimethoxy-3-oxo-propenyl-2-yl) phenyl groups or benzo [1, 2, 3] thiadiazole-7-yl groups are in Table 3.

TABLE 3

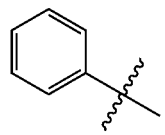

unsubstituted
Phenyl group

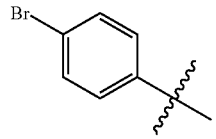

4-bromophenyl
group

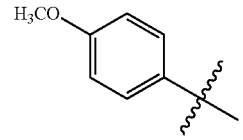

4-methoxyphenyl
group

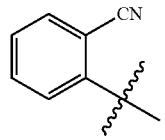

2-cyanophenyl
group

TABLE 3-continued

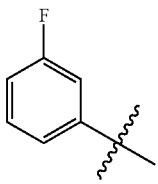

3-fluoro phenyl

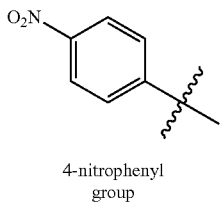 [SMILES: *c1ccc([N+](=O)[O-])cc1]

4-nitrophenyl group

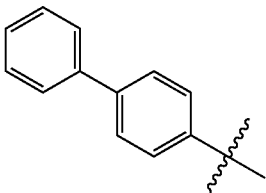

4-phenylphenyl group

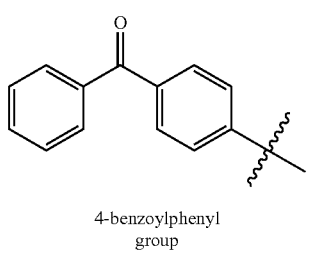 [SMILES: *c1ccc(C(=O)c2ccccc2)cc1]

4-benzoylphenyl group

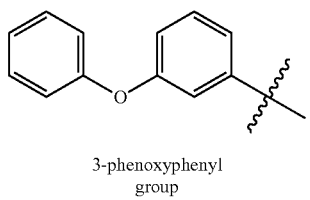 [SMILES: *c1cccc(Oc2ccccc2)c1]

3-phenoxyphenyl group

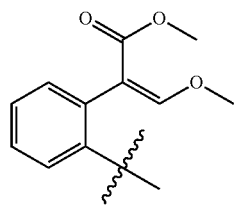

2-(1, 3-dimethoxy-3-oxo-pro penyl-2-yl) phenyl group

TABLE 3-continued

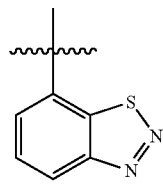

benzo [1,2,3] thiadiazole-7-yl group

As a carbon-nitrogen double bond causes geometrical isomerism, the intermediate compound further contains a Z isomer, an E isomer or a mixture, In order to further improve the dehydration performance of the intermediate compound and reduce the synthesis difficulty, substituents in the structure represented by the formula (VI) are further preferably selected. In a preferred embodiment, the W is selected from, but not limited to any one of $W^1$-$W^{84}$, the structure of which is in the Table 2, wherein $X^1$, $X^2$, $X^3$, $X^4$, $X^5$, $X^6$, $X^7$, $X^8$, $X^9$ independently include, but not limited to, hydrogen, halogens, cyano groups, nitro groups, —$SF_5$, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, $C_1$-$C_8$ alkoxy groups, $C_1$-$C_8$ alkyl groups, —$OR^3$, —$C(=O)OR^3$, —$N(R^4)S(=O)_2R^5$, —$S(=O)_2NR^3R^5$, —$N(R^4)C(=O)OR^3$, —$CR^4=NOR^3$, —$CH_2ON=C(CN)_2$, —$C(=O)SR^3$, —$C(=S)OR^3$, —$C(=S)SR^3$, —$CR^4=NR^5$, —$CR^4=N—NR^3R^5$, —$OSiR^4R^5R^6$, —$OC(=O)R^4$, —$OC(=O)OR^3$, —$OC(=O)NR^3R^4$, —$OC(=S)NR^3R^4$, —$NR^3R^4$, —$N(R^4)C(=O)NR^3R^5$, —$N(R^4)C(=S)NR^3R^5$, —$N=CR^4R^5$, —$N=C—NR^3R^4$, —$N(R^4)C(=NR^5)NR^3R^6$, —$N(R^4)OR^3$, —$N(R^4)NR^3R^5$, —$N=NR^4$, —$N(R^4)S(=O)R^5$, —$N(R^4)S(=O)_2OR^3$, —$N(R^4)S(=O)OR^3$, —$N(R^4)S(=O)NR^3R^5$, —$N(R^4)S(=O)_2NR^3R^5$, $NR^4C(=O)R^5$, —$SR^3$, —$S(=O)_2R^4$, —$S(=O)R^4$, —$S(=O)OR^3$, —$S(=O)NR^3R^4$, —$S(=O)_2OR^3$, —$S(=O)NR^3R^4$, —$SiR^3R^4R^5$, a group $G^1$ or a group $G^1$ optionally substituted with a substituent $J^1$, wherein the group $G^1$ is selected from phenyl groups, pyridyl groups, pyrazolyl groups, thiazolyl groups, isothiazolyl groups or thiadiazolyl groups, and the substitutent $J^1$ is selected from halogens, cyano groups, nitro groups, $C_1$-$C_8$ alkyl groups, $C_1$-$C_8$ haloalkyl groups, $C_1$-$C_8$ alkoxy groups, $C_1$-$C_8$ haloalkoxy groups, $C_1$-$C_8$ alkylthio groups or $C_1$-$C_8$ haloalkylthio groups;

Z is selected from, but not limited to, hydrogen, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, aryl groups, $C_1$-$C_8$ alkyl groups substituted with aryl groups, $C_1$-$C_8$ alkyl groups substituted with $C_1$-$C_8$ alkoxy groups, —$C(=O)R^3$ or —$C(=O)OR^3$;

K is selected from, but not limited to, oxygen, sulfur, $NR^3$, N—$OR^4$ or N—$NR^3R^4$;

$R^3$ is selected from, but not limited to, hydrogen, $C_1$-$C_8$ alkyl groups, $C_1$-$C_8$ haloalkyl groups, $C_3$-$C_6$ cycloalkyl groups, $C_1$-$C_8$ alkoxycarbonyl groups, $C_2$-$C_8$ alkenyl groups, $C_2$-$C_8$ haloalkenyl groups, $C_2$-$C_8$ alkynyl groups, $C_2$-$C_8$ haloalkynyl groups, the group $G^2$ or the group $G^2$ optionally substituted with the substitutent $J^2$, wherein the group $G^2$ is selected from, but not limited to, phenyl groups, pyridyl groups, pyrazolyl groups, thiazolyl groups, isothiazolyl groups or thiadiazolyl groups, and the substituent $J^2$ is selected from, but not limited to, halogens, cyano groups, nitro groups, hydroxyl groups, thiol groups, amino groups, —$CONH_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, amino groups substituted with $C_1$-$C_3$ alkyl, amino groups substituted with $C_1$-$C_3$ dialkyl, amino groups substituted with $C_3$-$C_6$ cycloalkyl, $C_1$-$C_3$ alkoxycarbonyl groups, $C_1$-$C_3$ alkylsulphonyl groups, aminocarbonyl groups substituted with $C_1$-$C_3$ alkyl or sulfonamide groups substituted with $C_1$-$C_3$ alkyl;

$R^4$, $R^5$ and $R^6$ independently include, but not limited to, hydrogen, $C_1$-$C_8$ alkyl groups, $C_1$-$C_8$ haloalkyl groups, $C_3$-$C_6$ cycloalkyl groups, $C_1$-$C_8$ alkoxy groups, $C_1$-$C_8$ haloalkoxy groups, $C_1$-$C_8$ alkoxycarbonyl groups, $C_2$-$C_8$ alkenyl groups, $C_2$-$C_8$ haloalkenyl groups, $C_2$-$C_8$ alkynyl groups, $C_2$-$C_8$ haloalkynyl groups, the group $G^3$ or the group $G^3$ optionally substituted with the substituent $J^3$, wherein the group $G^3$ is selected from, but not limited to, phenyl groups, pyridyl groups, pyrazolyl groups, thiazolyl groups, isothiazolyl groups or thiadiazolyl groups, and the substituent $J^3$ is selected from, but not limited to, halogens, cyano groups, nitro groups, hydroxyl groups, thiol groups, amino groups, —$CONH_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, $C_1$-$C_3$ alkylamino groups, $C_1$-$C_3$ dialkylamino groups, $C_3$-$C_6$ cycloalkylamino groups, $C_1$-$C_3$ alkoxycarbonyl groups, $C_1$-$C_3$ alkylsulphonyl groups, $C_1$-$C_3$ alkylaminocarbonyl groups or $C_1$-$C_3$ alkylaminosulfonyl groups;

Q is selected from, but not limited to, the group $G^4$ or the group $G^4$ optionally substituted with the substituent $J^4$, the group $G^4$ is selected from, but not limited to, phenyl groups, pyridyl groups, pyrazolyl groups, thiazolyl groups, isothiazolyl groups or thiadiazolyl groups, and the substituent $J^4$ is selected from, but not limited to, halogens, cyano groups, nitro groups, hydroxyl groups, thiol groups, amino groups, —$CONH_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, $C_1$-$C_3$ alkylamino groups, $C_1$-$C_3$ dialkylamino groups, $C_3$-$C_6$ cycloalkylamino groups, $C_1$-$C_3$ alkoxycarbonyl groups, $C_1$-$C_3$ alkylsulphonyl groups, $C_1$-$C_3$ alkylaminocarbonyl groups or $C_1$-$C_3$ alkylaminosulfonyl groups; and T is selected from, but not limited to, cyano groups, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, the group $G^5$ or the group $G^5$ optionally substituted with the substituent $J^5$, wherein the group $G^5$ is selected from, but not limited to, phenyl groups, pyridyl groups, pyrazolyl groups, thiazolyl groups, isothiazolyl groups or thiadiazolyl groups, and the substituent $J^5$ is selected from, but not limited to, halogens, cyano groups, nitro groups, hydroxyl groups, thiol groups, amino groups, —$CONH_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, $C_1$-$C_3$ alkylamino groups, $C_1$-$C_3$ dialkylamino groups, $C_3$-$C_6$ cycloalkylamino groups, $C_1$-$C_3$ alkoxycarbonyl groups, $C_1$-$C_3$ alkylsulphonyl groups, $C_1$-$C_3$ alkylaminocarbonyl groups or $C_1$-$C_3$ alkylaminosulfonyl groups, but the W is not selected from the following groups: unsubstituted phenyl groups, 4-bromophenyl groups, 4-methoxyphenyl groups, 2-cyanophenyl groups, 3-fluorophenyl groups, 4-nitrophenyl groups, 4-phenylphenyl, 4-benzoylphenyl groups, 3-phenoxyphenyl groups and 2-(1, 3-dimethoxy-3-oxo-propenyl-2-yl) phenyl groups or benzo [1, 2, 3] thiadiazole-7-yl groups.

In a preferred embodiment, the W is selected from, but not limited to $W^1$, $W^2$, $W^3$, $W^4$, $W^{12}$, $W^{16}$, $W^{18}$, $W^{21}$, $W^{48}$, $W^{58}$, $W^{59}$, $W^{67}$, $W^{68}$, $W^{69}$, $W^{70}$, $W^{71}$, $W^{72}$, $W^{74}$, $W^{79}$, $W^{80}$, $W^{81}$, $W^{82}$ or $W^{83}$;

$X^1$, $X^2$, $X^3$, $X^4$, $X^5$, $X^6$, $X^7$, $X^8$ and $X^9$ independently comprise, but not limited to, hydrogen, fluorine, chlorine, bromine, cyano groups, nitro groups, methyl groups, ethyl groups, isopropyl groups, chloromethyl groups, bromomethyl groups, difluoromethyl groups, trifluoromethyl groups, heptafluoroisopropyl groups, —$OR^3$, —$C(=O)OR^3$, —$N(R^4)S(=O)_2R^5$, —$S(=O)_2$ $NR^3R^4$, —$N(R^4)C(=O)OR^3$, —$CR^4=NOR^3$, —$CH_2ON=C(CN)_2$, $NR^4C(=O)R^5$, the group $G^1$ or the group $G^1$ optionally substituted with the substituent $J^1$, wherein the group $G^1$ is selected from, but not limited to, phenyl groups or pyridyl groups, and the substituent $J^1$ is halogens, cyano groups, nitro groups, trifluoromethyl groups, heptafluoropropyl groups, heptafluoroisopropyl groups, methoxy groups or trifluoromethoxy groups;

Z is selected from, but not limited to, hydrogen, methyl groups or benzyl groups;

K is oxygen;

$R^3$ is selected from, but not limited to, hydrogen, methyl groups, ethyl groups, propyl groups, isopropyl groups, cyclopropyl groups, difluoromethyl groups, trifluoromethyl groups, heptafluoropropyl groups, heptafluoroisopropyl groups, methoxycarbonyl groups, the group $G^2$ or the group $G^2$ optionally substituted with the substituent $J^2$, wherein the group $G^2$ is selected from, but not limited to, phenyl groups and pyridyl groups, and the substituent $J^2$ is halogens, cyano groups, nitro groups or trifluoromethyl groups;

$R^4$ and $R^5$ independently include, but not limited to, hydrogen, methyl groups, ethyl groups, propyl groups, isopropyl groups, cyclopropyl groups, difluoromethyl groups, trifluoromethyl groups, heptafluoropropyl groups, heptafluoroisopropyl groups, methoxy groups, trifluoromethoxy groups, methoxycarbonyl groups, the group $G^3$ or the group $G^3$ optionally substituted with the substituent $J^3$, wherein the group $G^3$ is selected from, but not limited to, phenyl groups and pyridyl groups, and the substituent $J^3$ is halogens, cyano groups, nitro groups, methyl groups, ethyl groups, propyl groups, chloromethyl groups, bromomethyl groups, trifluoromethyl groups, heptafluoroisopropyl groups, methoxy groups or trifluoromethoxy groups;

Q is selected from, but not limited to, $Q^1$, $Q^2$, $Q^3$, $Q^4$, $Q^5$, $Q^6$, $Q^7$, $Q^8$, $Q^9$, $Q^{10}$, phenyl groups, pyridyl groups or the group $G^4$ optionally substituted with the substituent $J^4$, wherein the group $G^4$ is selected from, but not limited to, phenyl groups or pyridyl groups, and the substituent $J^4$ is halogens, cyano groups, nitro groups, hydroxyl groups, thiol groups, amino groups, chloromethyl groups, bromomethyl groups, difluoromethyl groups, trifluoromethyl groups, heptafluoroisopropyl groups, methoxy groups, ethoxy groups, propoxy groups, isopropoxy groups, trifluoromethoxy groups, methylthio groups, ethylthio groups, trifluoromethylthio groups and trifluoroethylthio groups, wherein structures of $Q^1$-$Q^{10}$ are in Table 3; and T is selected from, but not limited to, cyano groups, methyl groups, ethyl groups, propyl groups, isopropyl groups, cyclopropyl groups, trifluoroethyl groups, difluoroethyl groups, cyclopropyl groups, cyclobutyl groups, cyclopentyl groups, cyclohexyl groups, the group $G^5$ or the group $G^5$ optionally substituted with the substitutent $J^5$, wherein the group $G^5$ is selected from, but not limited to, phenyl groups and pyridyl groups, and the substitutent $J^5$ is halogens, cyano groups, nitro groups, methyl groups, ethyl groups, propyl groups, isopropyl groups, chloromethyl groups, bromomethyl groups, trifluoromethyl groups, heptafluoroisopropyl groups, cyclopropyl groups, cyclobutyl groups, cyclopentyl groups, cyclohexyl groups, methoxy groups, ethoxy groups, propoxy groups, isopropoxy groups, trifluoromethoxy groups, methylthio groups, ethylthio groups, trifluoromethylthio groups or trifluoroethylthio groups.

Further preferably, the W is selected from, but not limited to, $W^1$, $W^2$, $W^3$, $W^4$, $W^{16}$, $W^{18}$, $W^{59}$ or $W^{69}$.

In the technical solution of the present disclosure, an important intermediate (VI) compound for preparing the malononitrile oxime ether compound (VII) is represented in Table 4, but is not limited to just the compounds.

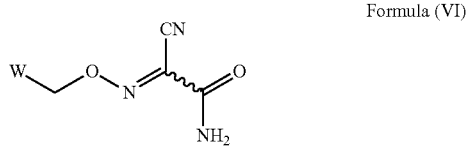

Formula (VI)

TABLE 4

| No. | |
|---|---|
| 1 | 4-CF$_3$S-Ph |
| 2 | 2-Cl-Ph |
| 3 | 3-Cl-Ph |
| 4 | 4-Cl-Ph |
| 5 | 2-F-Ph |
| 6 | 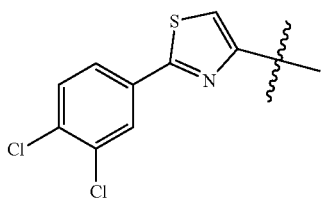 [SMILES: *c1csc(-c2ccc(Cl)c(Cl)c2)n1] |
| 7 | 4-F-Ph |
| 8 | 2-Br-Ph |
| 9 | 3-Br-Ph |
| 10 | 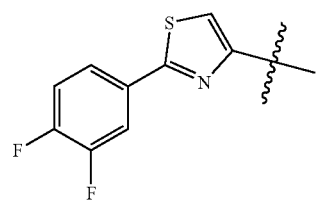 [SMILES: *c1csc(-c2ccc(F)c(Cl)c2)n1] |

TABLE 4-continued

| No. | |
|---|---|
| 11 | 2-I-Ph |
| 12 | 3-I-Ph |
| 13 | 4-I-Ph |
| 14 | 2-Me-Ph |
| 15 | 3-Me-Ph |
| 16 | 4-Me-Ph |
| 17 | 2-MeO-Ph |
| 18 | 3-MeO-Ph |
| 19 | 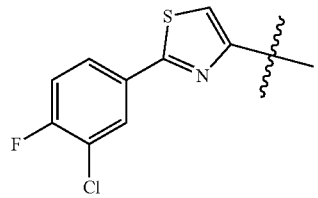 |
| 20 | 2-CF$_3$-Ph |
| 21 | 3-CF$_3$-Ph |
| 22 | 4-CF$_3$-Ph |
| 23 | 2-CF$_3$O-Ph |
| 24 | 3-CF$_3$O-Ph |
| 25 | 6-Cl-2-pyridyl |
| 26 | 2-Cl-3-pyridyl |
| 27 | 4-Cl-3-pyridyl |
| 28 | 5-Cl-3-pyridyl |
| 29 | 6-Cl-3-pyridyl |
| 30 | 2-Cl-4-pyridyl |
| 31 | 3-Cl-4-pyridyl |
| 32 | 1-naphthyl |
| 33 | 2,4-diCl-Ph |
| 34 | 2,6-diCl-Ph |
| 35 | 3,4-diCl-Ph |
| 36 | 3,5-diCl-Ph |
| 37 | 2-Cl-6-F-Ph |
| 38 | 2-Cl-4-Me-Ph |
| 39 | 2,4-di(MeO)-Ph |
| 40 | 2-Cl-4-Et-Ph |
| 41 | 2-Cl-5-NO$_2$-Ph |
| 42 | 3-Cl-4-Me-Ph |
| 43 | 4-Cl-3-Me-Ph |
| 44 | 2-F-4-Me-Ph |
| 45 | 2,3,4,5,6-5F-Ph |
| 46 | 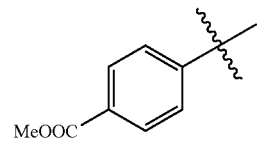 [SMILES: *c1ccc(C(=O)OC)cc1] |
| 47 | 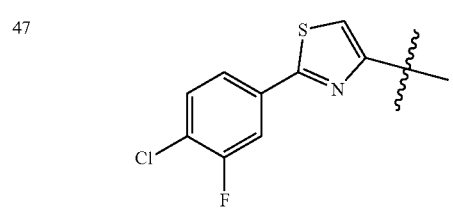 |
| 48 | 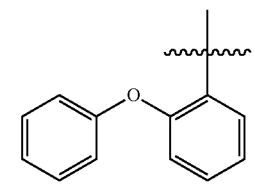 [SMILES: *c1ccccc1Oc1ccccc1] |

TABLE 4-continued
| No. | |
|---|---|
| 49 | 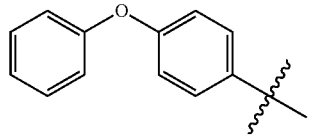 [SMILES: *c1ccc(Oc2ccccc2)cc1] |
| 50 | 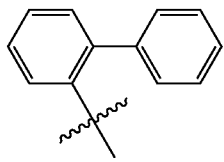 [SMILES: *c1ccccc1-c1ccccc1] |
| 51 | 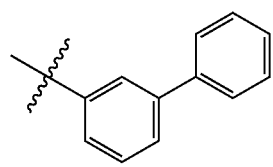 [SMILES: *c1cccc(-c2ccccc2)c1] |
| 52 | 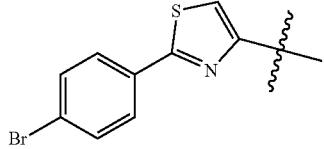 |
| 53 | 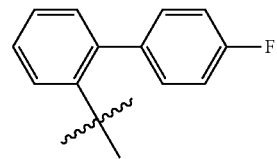 [SMILES: *c1ccccc1-c1ccc(F)cc1] |
| 54 | 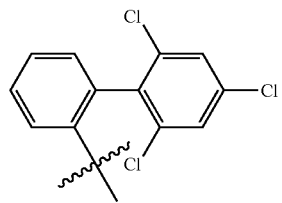 [SMILES: *c1ccccc1-c1c(Cl)cc(Cl)cc1Cl] |
| 55 | 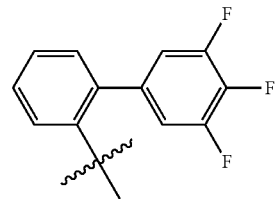 [SMILES: *c1ccccc1-c1cc(F)c(F)c(F)c1] |
| 56 | 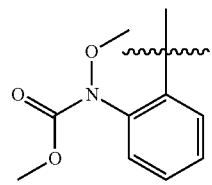 [SMILES: *c1ccccc1N(OC)C(=O)OC] |
| 57 | 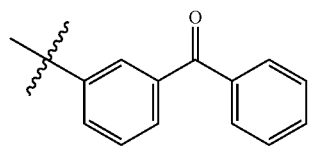 [SMILES: *c1cccc(C(=O)c2ccccc2)c1] |
TABLE 4-continued
| No. | |
|---|---|
| 58 | 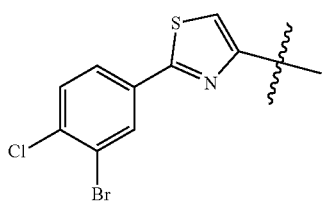 [SMILES: *c1csc(-c2ccc(Cl)c(Br)c2)n1] |
| 59 | 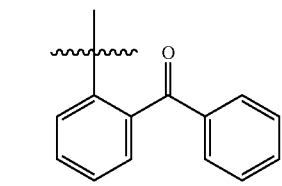 [SMILES: *c1ccccc1C(=O)c1ccccc1] |
| 60 | 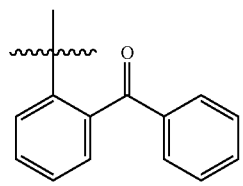 |
| 61 | 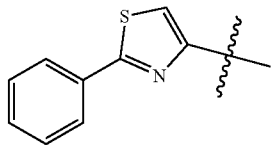 [SMILES: *c1csc(-c2ccccc2)n1] |
| 62 | 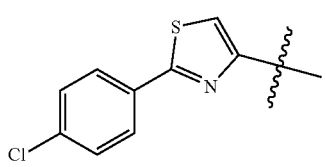 [SMILES: *c1csc(-c2ccc(Cl)cc2)n1] |
| 63 | 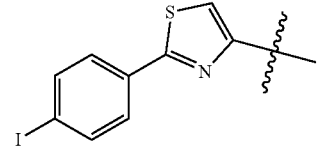 [SMILES: *c1csc(-c2ccc(I)cc2)n1] |
| 64 | 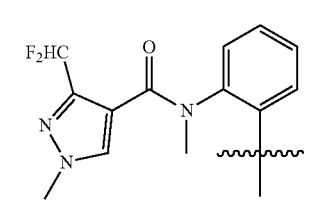 [SMILES: *c1ccccc1N(C)C(=O)c1cn(C)nc1C(F)F] |
| 65 | 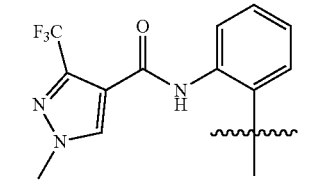 [SMILES: *c1ccccc1NC(=O)c1cn(C)nc1C(F)(F)F] |

TABLE 4-continued

| No. | Structure |
|---|---|
| 66 | (structure) |
| 67 | (structure) |
| 68 | (structure) |
| 69 | (structure) |
| 70 | (structure) |
| 71 | (structure) |
| 72 | (structure) |
| 73 | (structure) |
| 74 | (structure) |
| 75 | (structure) |
| 76 | (structure) |
| 77 | (structure) |
| 78 | (structure) |
| 79 | (structure) |
| 80 | (structure) |
| 81 | (structure) |

TABLE 4-continued
| No. | |
|---|---|
| 82 | 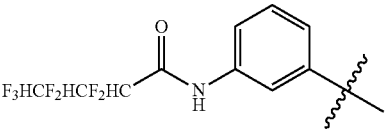 |
| 83 | 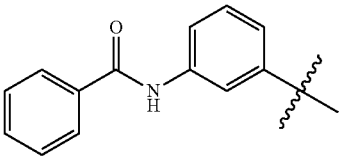 [SMILES: *c1cccc(NC(=O)c2ccccc2)c1] |
| 84 | 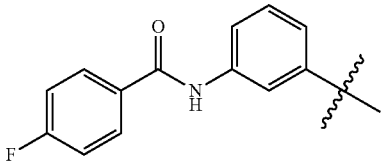 [SMILES: *c1cccc(NC(=O)c2ccc(F)cc2)c1] |
| 85 | 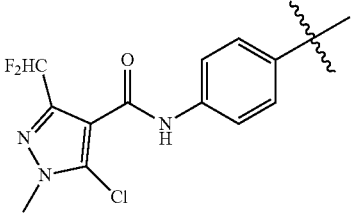 [SMILES: *c1ccc(NC(=O)c2c(C(F)F)nn(C)c2Cl)cc1] |
| 86 | 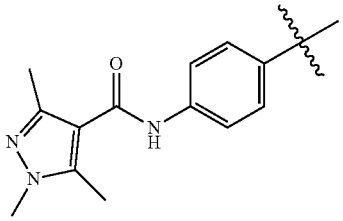 [SMILES: *c1ccc(NC(=O)c2c(C)nn(C)c2C)cc1] |
| 87 | 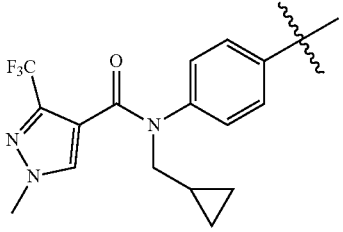 [SMILES: *c1ccc(N(CC2CC2)C(=O)c2cn(C)nc2C(F)(F)F)cc1] |
| 88 | 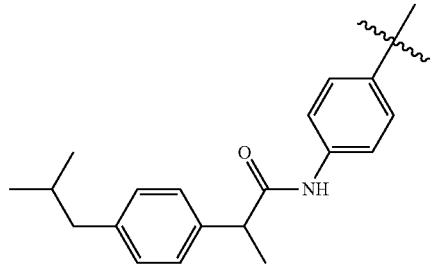 [SMILES: *c1ccc(NC(=O)C(C)c2ccc(CC(C)C)cc2)cc1] |
| 89 | 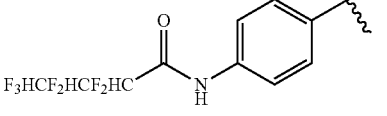 |
| 90 | 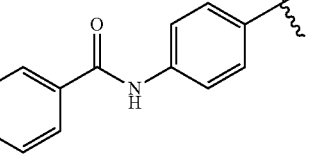 |
| 91 | 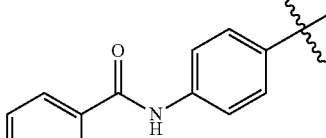 |
| 92 | 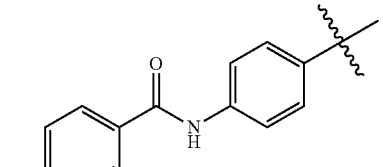 |
| 93 | 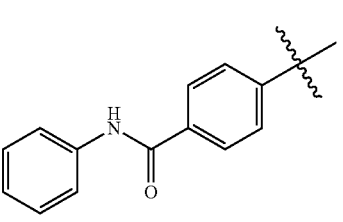 [SMILES: *c1ccc(C(=O)Nc2ccccc2)cc1] |
| 94 | 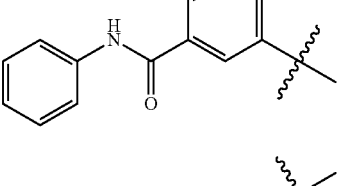 |
| 95 | 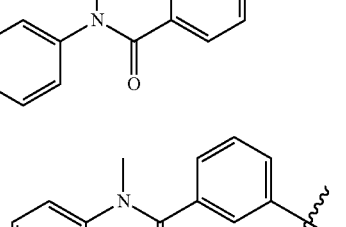 |
| 96 | 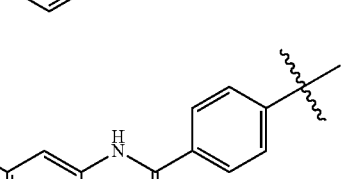 |

TABLE 4-continued
| No. | |
|---|---|
| 97 | 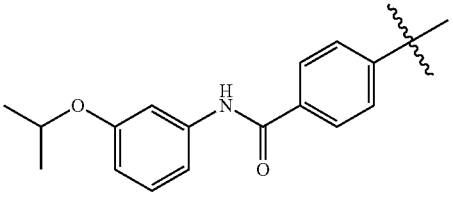 [SMILES: *c1ccc(C(=O)Nc2cccc(OC(C)C)c2)cc1] |
| 98 | 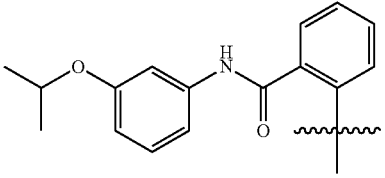 |
| 99 | 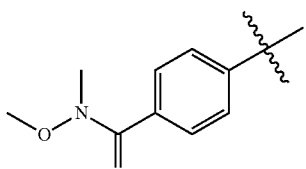 |
| 100 | 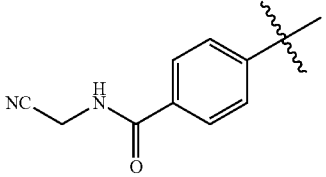 [SMILES: *c1ccc(C(=O)NCC#N)cc1] |
| 101 | 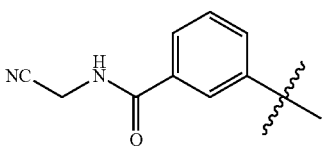 [SMILES: *c1cccc(C(=O)NCC#N)c1] |
| 102 | 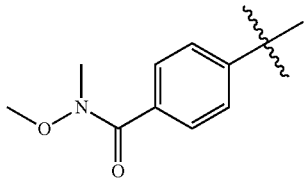 [SMILES: *c1ccc(C(=O)N(C)OC)cc1] |
| 103 | 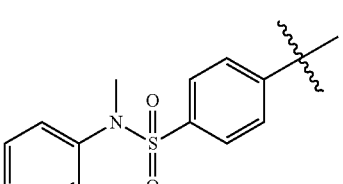 |
| 104 | 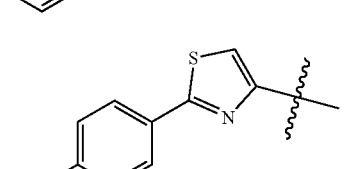 |
| 105 | 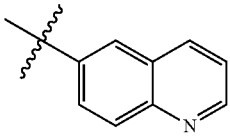 [SMILES: *c1ccc2ncccc2c1] |
| 106 | 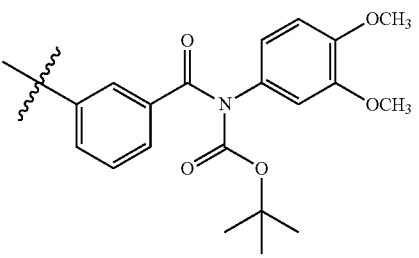 [SMILES: *c1cccc(C(=O)N(C(=O)OC(C)(C)C)c2ccc(OC)c(OC)c2)c1] |
| 107 | 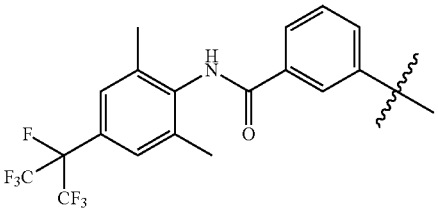 [SMILES: *c1cccc(C(=O)Nc2c(C)cc(C(F)(C(F)(F)F)C(F)(F)F)cc2C)c1] |
| 108 | 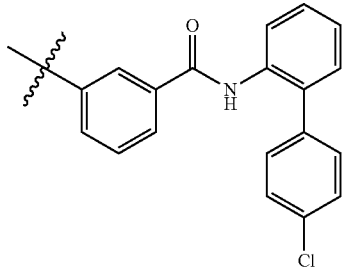 [SMILES: *c1cccc(C(=O)Nc2ccccc2-c2ccc(Cl)cc2)c1] |
| 109 | 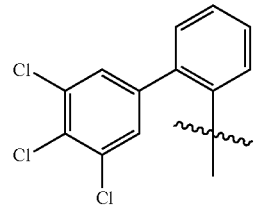 [SMILES: *c1ccccc1-c1cc(Cl)c(Cl)c(Cl)c1] |
| 110 | 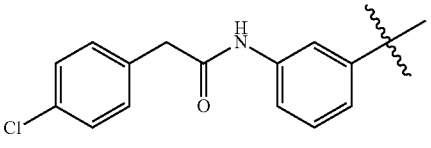 [SMILES: *c1cccc(NC(=O)Cc2ccc(Cl)cc2)c1] |
| 111 | 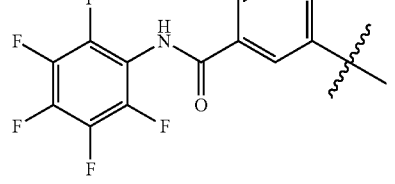 |

TABLE 4-continued
| No. | |
|---|---|
| 112 | 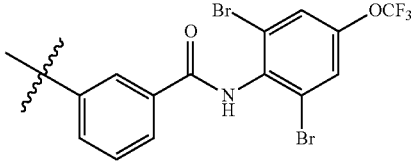 [SMILES: *c1cccc(C(=O)Nc2c(Br)cc(OC(F)(F)F)cc2Br)c1] |
| 113 | 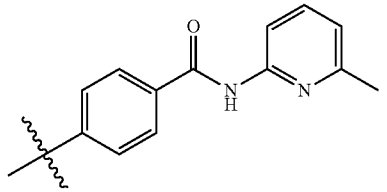 [SMILES: *c1ccc(C(=O)Nc2cccc(C)n2)cc1] |
| 114 | 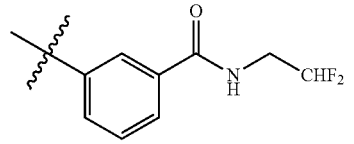 [SMILES: *c1cccc(C(=O)NCC(F)F)c1] |
| 115 | 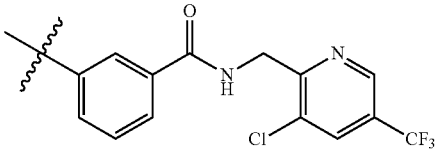 [SMILES: *c1cccc(C(=O)NCc2ncc(C(F)(F)F)cc2Cl)c1] |
| 116 | 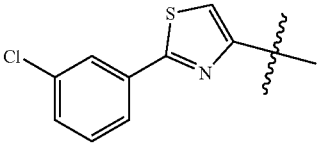 [SMILES: *c1csc(-c2cccc(Cl)c2)n1] |
| 117 | 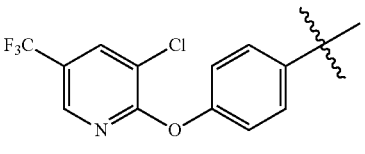 [SMILES: *c1ccc(Oc2ncc(C(F)(F)F)cc2Cl)cc1] |
| 118 | 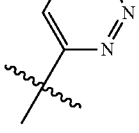 |
| 119 | 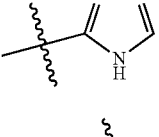 |
| 120 | 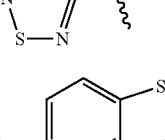 |
| 121 | 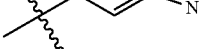 |
| 122 | 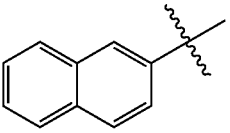 [SMILES: *c1ccc2ccccc2c1] |
| 123 | 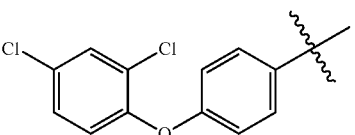 |
| 124 | 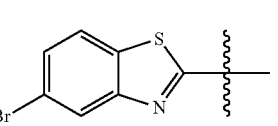 |
| 125 | 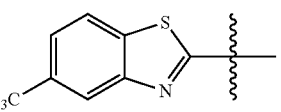 |
| 126 | 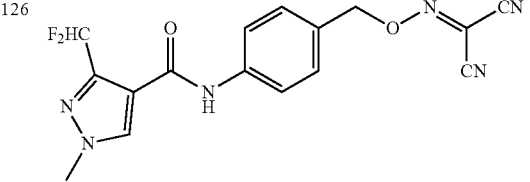 |
| 127 | 3,4-diBr-Ph |
| 128 | 3-F-4-Cl-Ph |
| 129 | 3-I-4-Cl-Ph |
| 130 | 3-Cl-4-Br-Ph |
| 131 | 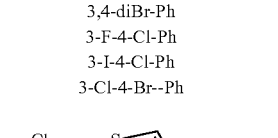 |
| 132 | 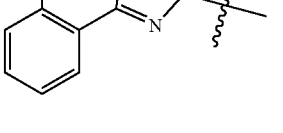 |
| 133 | 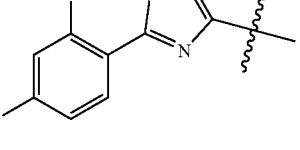 |
| 134 | 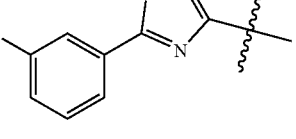 |

TABLE 4-continued

| No. | |
|---|---|
| 135 | 2-(3-F₃CO-phenyl)-thiazol-4-yl |
| 136 | 2-(4-F₃CO-phenyl)-thiazol-4-yl |
| 137 | 2-(4-F-phenyl)-thiazol-5-yl |
| 138 | 2-(2-Cl-phenyl)-thiazol-5-yl |
| 139 | 2-(2-F-phenyl)-thiazol-5-yl |
| 140 | 2-(2-CF₃-phenyl)-thiazol-5-yl |
| 141 | 4-CF₃O-Ph |
| 142 | 2-CHF₂O-Ph |
| 143 | 3-CHF₂-O-Ph |
| 144 | 4-CHF₂O-Ph |
| 145 | 2-(CF₃)₂CF-Ph |
| 146 | 3-(CF₃)₂CF-Ph |
| 147 | 4-(CF₃)₂CF-Ph |
| 148 | 2-NO₂-Ph |
| 149 | 3-NO₂-Ph |
| 150 | 2-(3,4-diBr-phenyl)-thiazol-4-yl |
| 151 | 2-(2,6-diF-phenyl)-thiazol-4-yl |
| 152 | 3-CN-Ph |
| 153 | 4-CN-Ph |
| 154 | 2-N(CH₃)₂-Ph |
| 155 | 3-N(CH₃)₂-Ph |
| 156 | 4-N(CH₃)₂-Ph |
| 157 | 2-pyridyl |
| 158 | 3-pyridyl |
| 159 | 4-pyridyl |
| 160 | 2-Furyl |
| 161 | 2-thiazolyl |
| 162 | 3-Cl-2-pyridyl |
| 163 | 4-Cl-2-pyridyl |
| 164 | 5-Cl-2-pyridyl |
| 165 | 2-F-4-CN-Ph |
| 166 | 3-F-4-Me-Ph |
| 167 | 2,4-diMe-Ph |
| 168 | 2,5-diMe-Ph |
| 169 | 3,4-diMe-Ph |
| 170 | 3,4-di(MeO)-Ph |
| 171 | 3,5-di(MeO)-Ph |
| 172 | 3,5-di(CF₃)-Ph |
| 173 | 2,5-diCl-4-F-Ph |
| 174 | 2,4,5-triCl-Ph |
| 175 | 2,4,6-triCl-Ph |
| 176 | 2,4,6-triCH₃-Ph |
| 177 | 2-F-4-CN-Ph |
| 178 | 2,4-diF-Ph |
| 179 | 3,4-diF-Ph |
| 180 | 3,5-diF-Ph |
| 181 | 2,6-diF-Ph |
| 182 | 2,4,5-triF-Ph |
| 183 | 3,4,5-triF-Ph |
| 184 | 2,4,6-triF-Ph |
| 185 | 4-tert-butyl-phenyl |
| 186 | 4-HOOC-phenyl |
| 187 | 2-methyl-biphenyl-3-yl |

TABLE 4-continued
| No. | |
|---|---|
| 188 | 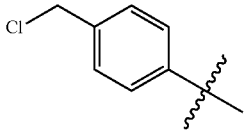 [SMILES: *c1ccc(CCl)cc1] |
| 189 | 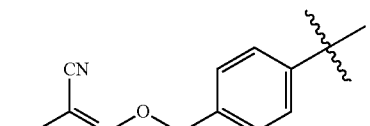 |
| 190 | 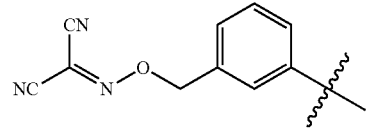 [SMILES: *c1cccc(CON=C(C#N)C#N)c1] |
| 191 | 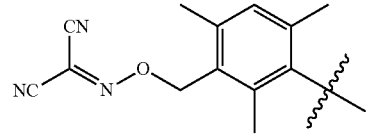 [SMILES: *c1c(C)cc(C)c(CON=C(C#N)C#N)c1C] |
| 192 | 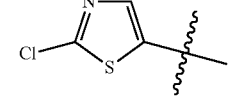 |
| 193 | 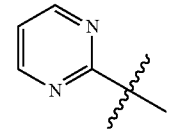 [SMILES: *c1ncccn1] |
| 194 | 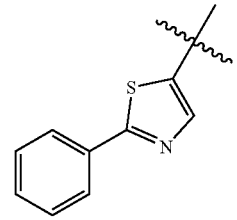 [SMILES: *c1cnc(-c2ccccc2)s1] |
| 195 | 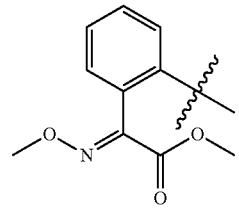 |
| 196 | 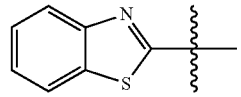 [SMILES: *c1nc2ccccc2s1] |
| 197 | 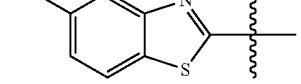 |
| 198 | 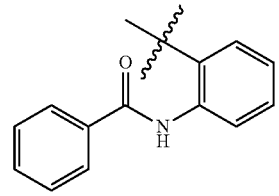 [SMILES: *c1ccccc1NC(=O)c1ccccc1] |
| 199 | 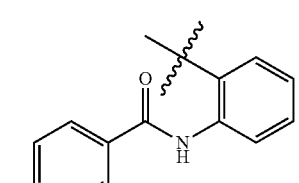 |
| 200 | 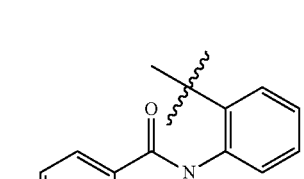 |
| 201 | 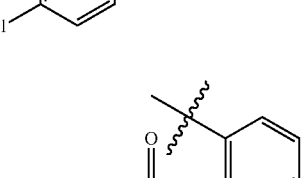 |
| 202 | 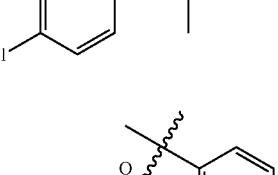 |
| 203 | 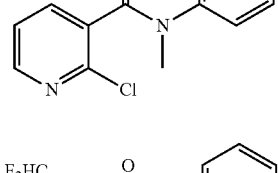 |
| 204 | 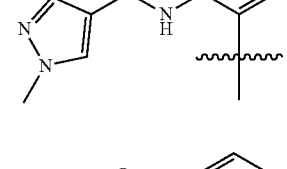 |

TABLE 4-continued
| No. | | No. | |
|---|---|---|---|
| 205 | 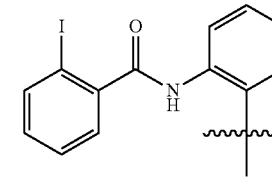 | 213 | 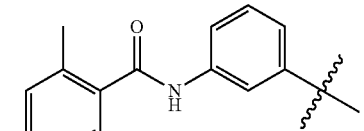 |
| 206 | 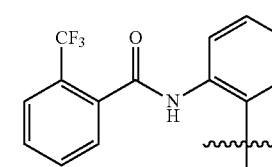 | 214 | 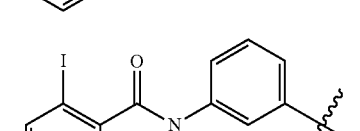 |
| 207 | 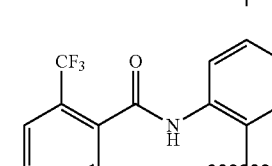 | 215 | 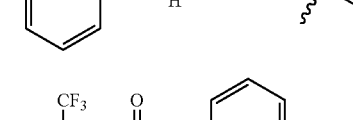 |
| 208 | 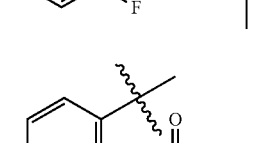 | 216 | 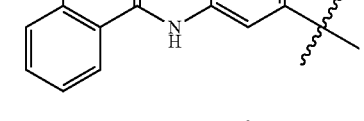 |
| 209 | 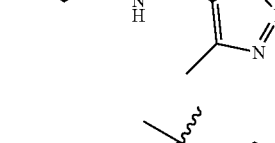 | 217 | 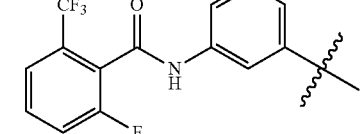 |
| 210 | 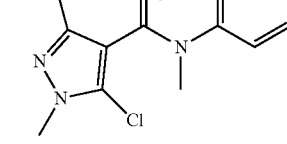 | 218 | 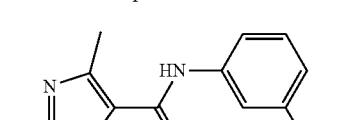 |
| 211 | 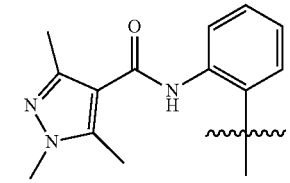 [SMILES: *c1ccccc1NC(=O)c1c(C)nn(C)c1C] | 219 | 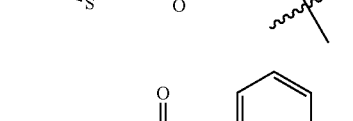 |
| 212 | 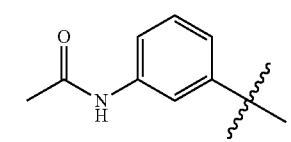 [SMILES: *c1cccc(NC(C)=O)c1] | 220 | 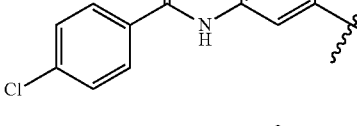 |
| | | 221 | 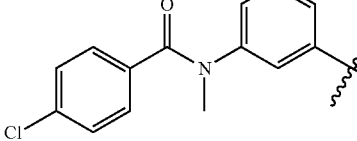 |

TABLE 4-continued
| No. | |
|---|---|
| 222 | 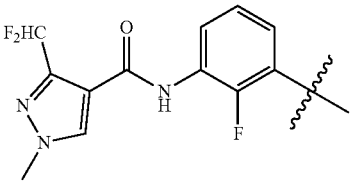 [SMILES: *c1cccc(NC(=O)c2cn(C)nc2C(F)F)c1C] |
| 223 | 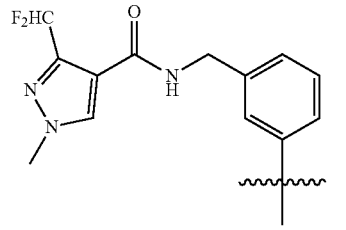 [SMILES: *c1cccc(CNC(=O)c2cn(C)nc2C(F)F)c1] |
| 224 | 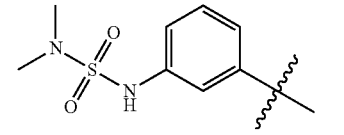 [SMILES: *c1cccc(NS(=O)(=O)N(C)C)c1] |
| 225 | 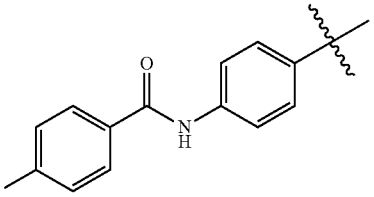 |
| 226 | 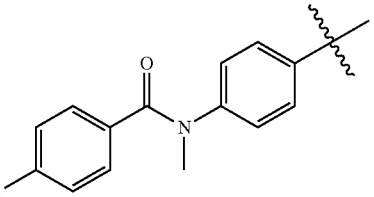 |
| 227 | 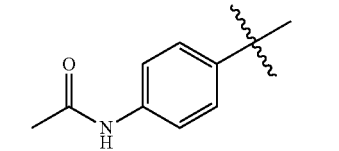 [SMILES: *c1ccc(NC(C)=O)cc1] |
| 228 | 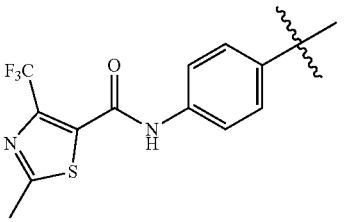 [SMILES: *c1ccc(NC(=O)c2sc(C)nc2C(F)(F)F)cc1] |
| 229 | 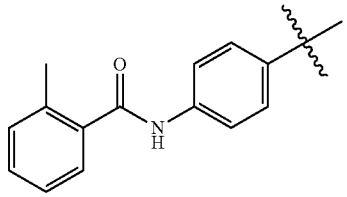 [SMILES: *c1ccc(NC(=O)c2ccccc2C)cc1] |
| 230 | 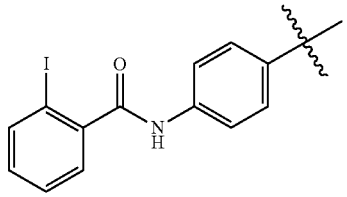 |
| 231 | 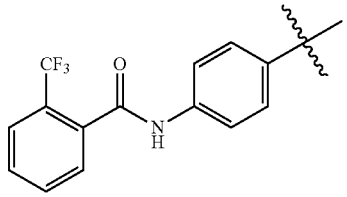 [SMILES: *c1ccc(NC(=O)c2ccccc2C(F)(F)F)cc1] |
| 232 | 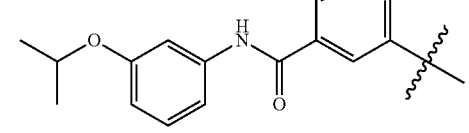 |
| 233 | 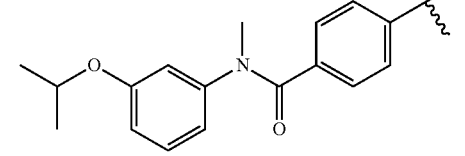 |
| 234 | 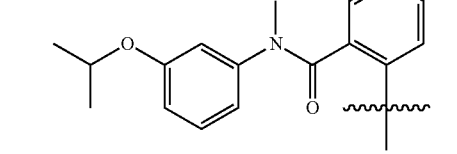 |
| 235 | 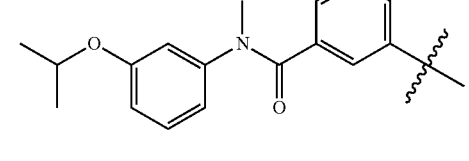 |
| 236 | 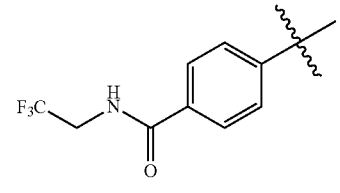 [SMILES: *c1ccc(C(=O)NCC(F)(F)F)cc1] |

TABLE 4-continued
| No. | |
|---|---|
| 237 | 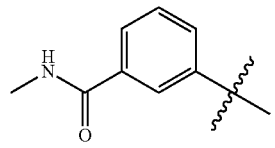 [SMILES: *c1cccc(C(=O)NC)c1] |
| 238 | 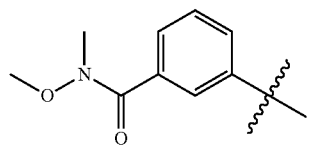 [SMILES: *c1cccc(C(=O)N(C)OC)c1] |
| 239 | 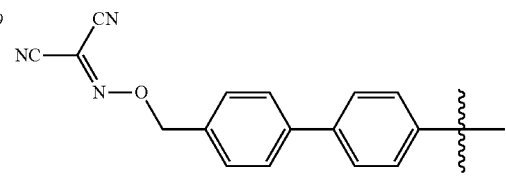 |
| 240 | 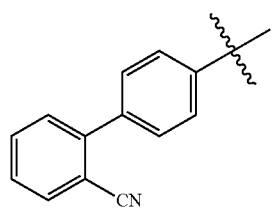 [SMILES: *c1ccc(-c2ccccc2C#N)cc1] |
| 241 | 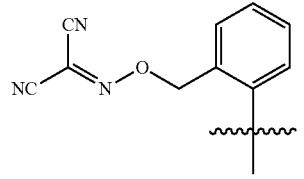 [SMILES: *c1ccccc1CON=C(C#N)C#N] |
| 242 | 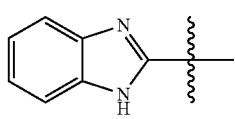 [SMILES: *c1nc2ccccc2[nH]1] |
| 243 | 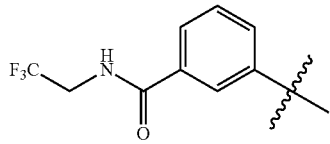 [SMILES: *c1cccc(C(=O)NCC(F)(F)F)c1] |
| 244 |  |
| 245 | 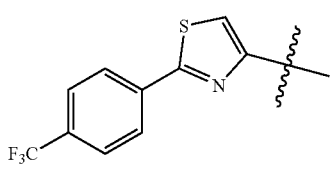 [SMILES: *c1csc(-c2ccc(C(F)(F)F)cc2)n1] |
TABLE 4-continued
| No. | |
|---|---|
| 246 | 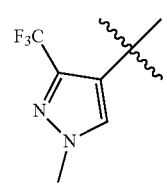 |
| 247 | 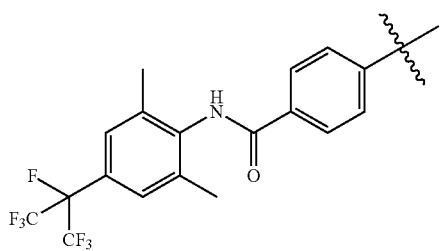 [SMILES: *c1ccc(C(=O)Nc2c(C)cc(C(F)(C(F)(F)F)C(F)(F)F)cc2C)cc1] |
| 248 | 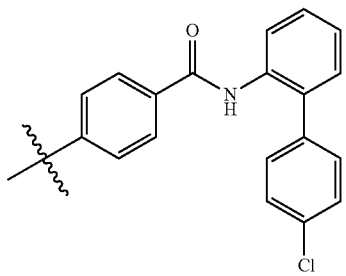 [SMILES: *c1ccc(C(=O)Nc2ccccc2-c2ccc(Cl)cc2)cc1] |
| 249 | 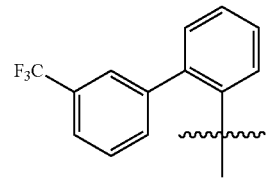 [SMILES: *c1ccccc1-c1cccc(C(F)(F)F)c1] |
| 250 | 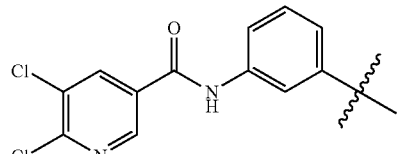 |
| 251 | 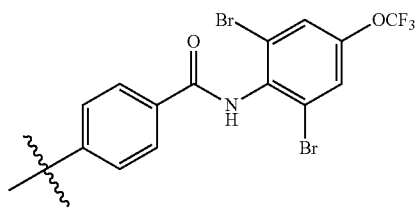 [SMILES: *c1ccc(C(=O)Nc2c(Br)cc(OC(F)(F)F)cc2Br)cc1] |
| 252 | 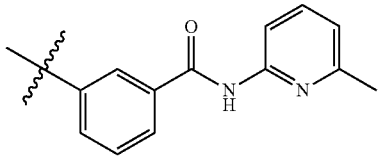 [SMILES: *c1cccc(C(=O)Nc2cccc(C)n2)c1] |

TABLE 4-continued

| No. | |
|---|---|
| 253 | 4-(N-(2,2-difluoroethyl)carbamoyl)phenyl group |
| 254 | 4-(N-((3-chloro-5-(trifluoromethyl)pyridin-2-yl)methyl)carbamoyl)phenyl group |
| 255 | 2-(3-fluorophenyl)thiazol-4-yl group |
| 256 | 2-(2-fluorophenyl)thiazol-4-yl group |
| 257 | 4-(pyridin-2-yloxy)phenyl group |
| 258 | 1-acetyl-1H-imidazol-5-yl group |
| 259 | 1,2,3-thiadiazol-4-yl group |
| 260 | 1H-indol-6-yl group |
| 261 | 1H-benzo[d]imidazol-5-yl group |
| 262 | naphthalen-1-yl group |
| 263 | 4-((5-(trifluoromethyl)pyridin-2-yl)oxy)phenyl group |
| 264 | 5-fluorobenzo[d]thiazol-2-yl group |
| 265 | 3-cyanopyridin-2-yl group |
| 266 | 5-iodobenzo[d]thiazol-2-yl group |
| 267 | 3,4-diI-Ph |
| 268 | 3-Br-4-Cl-Ph |
| 269 | 3-Cl-4-F--Ph |
| 270 | 3-Cl-4-I--Ph |
| 271 | 2-(2-chloro-4-fluorophenyl)thiazol-4-yl group |
| 272 | 2-(2-(trifluoromethyl)phenyl)thiazol-4-yl group |
| 273 | 2-(3-methoxyphenyl)thiazol-4-yl group |
| 274 | 2-(4-methoxyphenyl)thiazol-4-yl group |

TABLE 4-continued

| No. | Structure |
|-----|-----------|
| 275 | 2-(OCF3)phenyl-thiazole |
| 276 | 4-Cl-phenyl-thiazole |
| 277 | 4-CF3-phenyl-thiazole |
| 278 | 3-Cl-phenyl-thiazole |
| 279 | 3-F-phenyl-thiazole |
| 280 | 3-CF3-phenyl-thiazole |

TABLE 5

| Compound | Solvent | ¹HNMR(data) | Physical property |
|---|---|---|---|
| 9 | CDCl₃ | 7.54-7.52 (m, 2H), 7.32-7.29 (m, 2H), 6.39 (s, 1H), 5.92 (s, 1H), 5.39 (s, 2H). | White solid |
| 29 | CDCl₃ | 8.44 (s, 1H), 7.72 (d, 2H), 7.42 (d, 2H), 6.34 (s, 1H), 5.56 (s, 1H), 5.43 (s, 2H). | White solid |
| 35 | DMSO-d₆ | 8.08 (s, 1H), 8.00 (s, 1H), 7.81 (s, 1H), 7.70 (d, 1H), 7.50 (dd, 1H), 5.48 (s, 2H). | White solid |
| 60 | CDCl₃ | 7.95-7.93 (m, 2H), 7.46-7.45 (m, 3H), 7.36 (s, 1H), 6.52 (s, 1H), 5.68 (s, 1H), 5.61 (s, 2H). | White solid |
| 61 | CDCl₃ | 7.88 (d, 2H), 7.43(d, 2H), 7.37(s, 1H), 6.48 (s, 1H), 5.60 (s, 2H), 5.50 (s, 1H). | White solid |
| 105 | DMSO-d₆ | 8.94 (dd, 1H), 8.41 (t, 1H), 8.09 - 8.06 (m, 2H), 8.05 (s, 1H), 7.98 (s, 1H), 7.86 (d, 1H), 7.59-7.57 (m, 1H), 5.68 (s, 2H). | Yellow solid |
| 153 | CDCl₃ | 7.72 (d, 2H), 7.49 (d, 2H), 6.33 (s, 1H), 5.49 (s, 2H), 5.48 (s, 1H). | White solid |
| 187 | CDCl₃ | 7.44-7.41 (m, 2H), 7.38-7.35 (m, 1H), 7.33-7.32 (m, 1H), 7.30-7.27 (m, 4H), 6.42 (s, 1H), 5.85 (s, 1H), 5.54 (s, 2H), 2.27 (s, 3H). | White solid |
| 192 | CDCl₃ | 7.62 (s, 1H), 6.37 (s, 1H), 5.72 (s, 1H), 5.52 (s, 2H). | Pale Yellow solid |

In the above definitions of the compounds of the general formulas, the used terms are collected for representing the following substituents generally:

the term "unsubstituted" represents that all the substituents are hydrogen;

halogens: refer to fluorine, chlorine, bromine or iodine;

alkyl groups: linear or branched alkyl groups, for example, methyl groups, ethyl groups, n-propyl groups, isopropyl groups, or different butyl isomers, pentyl isomers or hexyl isomers;

haloalkyl groups: linear or branched alkyl groups, and hydrogen atoms on these alkyl groups may be partially or wholly substituted with halogens, for example, chloromethyl groups, dichloromethyl groups, trichloromethyl groups, fluoromethyl groups, difluoromethyl groups, trifluoromethyl groups, heptafluoroisopropyl groups and the like;

cycloalkyl groups: substituted or unsubstituted cyclic alkyl groups, for example, cyclopropyl groups, cyclopentyl groups or cyclohexyl groups, and the substituents, for example, methyl groups, halogens and the like;

alkenyl groups: include linear or branched alkenes, for example, vinyl groups, 1-propenyl groups, 2-propenyl groups and different butenyl isomers, pentenyl isomers and hexenyl isomers, and the alkenyl groups further include polyenes, for example, 1, 2-propadienyl groups and 2,4-hexadienyl groups;

haloalkenyl groups: alkenyl groups, at least one or more hydrogen atoms substituted with halogen atoms;

alkynyl groups: include linear or branched alkynes, for example, ethynyl groups, 1-propynyl groups and different butynyl isomers, pentynyl isomers and hexynyl isomers, and the alkynyl groups further include groups consisting of multiple triple bonds, for example, 2, 5-hexadiyne groups;

haloalkynyl groups: alkynyl groups, at least one or more hydrogen atoms of which may be substituted with halogen atoms;

alkoxy groups: linear or branched alkyl groups, bonded to the structures via oxygen atom bonds, for example, methoxy groups, ethoxy groups, t-butoxy groups and the like;

haloalkoxy groups: linear or branched alkoxy groups, and hydrogen atoms on these alkoxy groups may be partially or wholly substituted with the halogens, for example, chloromethoxy groups, dichloromethoxy groups, trichloromethoxy groups, fluoromethoxy groups, difluoromethoxy groups, trifluoromethoxy groups, chlorofluoromethoxy groups, trifluoroethoxy groups and the like;

alkylthio groups: the linear or branched alkyl groups, bonded to the structures via sulfur atom bonds, for example, methylthio groups, ethylthio groups and the like;

haloalkylthio groups: linear or branched alkylthio groups, and hydrogen atoms on these alkylthio groups may be partially or wholly substituted with the halogens, for example, difluoromethylthio groups, trifluroethylthio groups and the like;

alkylamino groups: linear or branched alkyl groups, bonded to the structures via nitrogen atom bonds, for example, methylamino groups, ethylamino groups, n-propylamino groups, isopropylamino groups and isomeric butyl amine;

dialkylamino groups: two same or different linear or branched alkyl groups, bonded to the structures via the nitrogen atom bonds, for example, dimethylamino groups, methylethylamino groups and the like;

cycloalkylamino groups: cycloalkyl-NH—, for example, cyclopropylamino groups;

alkylaminocarbonyl groups: alkyl-NH—CO—, for example, $CH_3NHCO$—;

alkylaminosulfonyl groups: alkyl-NH—S(O)$_2$—, for example, $CH_3NHS(O)_2$—;

alkoxyalkyl groups: alkyl-O-alkyl-, for example, $CH_3OCH_2$—;

haloalkoxyalkyl groups: linear or branched alkoxyalkyl groups, and hydrogen atoms on these alkoxyalkyl groups may be partially or wholly substituted with the halogens, for example, chloromethoxymethyl groups, dichloromethoxymethyl groups, trichloromethoxymethyl groups, fluoromethoxymethyl groups, difluoromethoxymethyl groups, trifluoromethoxymethyl groups, chlorofluoromethoxymethyl groups, trifluoroethoxymethyl groups and the like;

alkoxyalkoxy groups: alkyl-O-alkyl-O—, for example, $CH_3OCH_2O$—;

alkoxycarbonyl groups: alkyl-O—CO—, for example, $CH_3OCO$—;

alkylsulphonyl groups: alkyl-S(O)$_2$—, for example, methylsulfonyl groups;

aryl groups: monocyclic or polycyclic aromatic groups with 6-20 carbon atoms, for example, phenyl groups and naphthyl groups;

arylalkyl groups: aryl-alkyl-, for example, $PhCH_2$—; and heteroaryl groups: monocyclic or polycyclic heteroaromatic groups with 1-20 carbon atoms and 1-4 heteroatoms selected from N, S and O, for example, pyrrolyl groups, furyl groups, thienyl groups, imidazolyl groups, pyrazolyl groups, oxazolyl groups, thiazolyl groups, isoxazolyl groups, isothiazolyl groups, pyridyl groups, pyrimidinyl groups, pyridazinyl groups, pyridazinone groups, indolyl groups, benzofuranyl groups, benzoxazolyl groups, benzothienyl groups, benzothiazolyl groups, benzoisoxazolyl groups, benzoisothiazolyl groups, benzimidazolyl groups, benzopyrazolyl groups, quinoxalinyl groups and the like.

The present application will be further described in detail with reference to the specific embodiments below, and these examples should not be interpreted as limiting the claimed protective scope of the present application.

The compound IV in various examples may be purchased or may be prepared according to the method described in a literature "WO2017107939A1".

The compound V in various examples is prepared according to the method described in a literature "Journal of Coordination Chemistry, 57 (16), 1431-1445, 2004".

Embodiment 1

1) Preparation of 2-cyano-2-[((3, 4-dichlorophenyl)methoxy)imino] acetamide (compound 35)

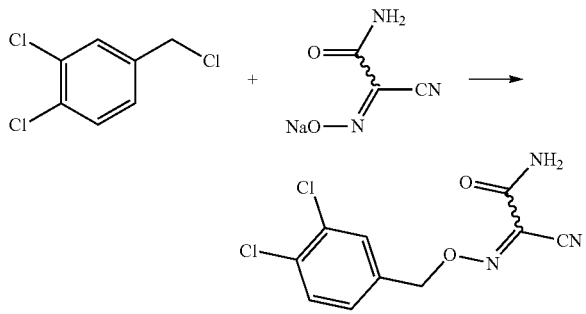

A mixture of 3, 4-dichlorobenzyl chloride (9.87 g, 50.0 mmol), 2-cyano-2-hydroximino acetamide sodium salt (10.66 g, 75.0 mmol), potassium iodide (0.84 g, 5.0 mmol) and acetonitrile (80 mL) was added into a reaction flask. The mixture was stirred at 80° C. for 10 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 35 (11.00 g, analysis by HNMR, isomers Z:E=1:1) as white solid with yield of 80% (calculated by 3, 4-dichlorobenzyl chloride).

$^1$HNMR (600 MHz, DMSO-d$_6$) δ(ppm): 8.08 (s, 1H), 8.00 (s, 1H), 7.81 (s, 1H), 7.70 (d, 1H), 7.50 (dd, 1H), 5.48 (s, 2H).

2) Preparation of 2-[((3, 4-dichlorophenyl)methoxy)imino] malononitrile

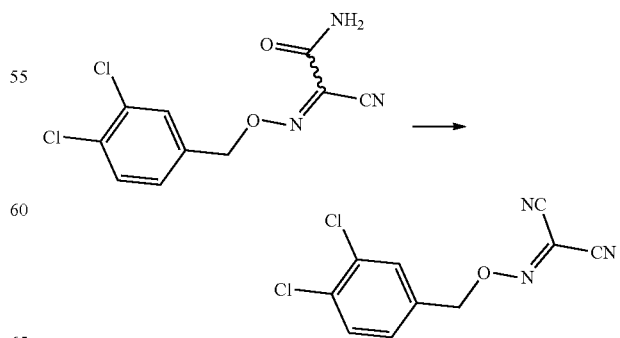

A mixture of 2-cyano-2-[((3, 4-dichlorophenyl)methoxy) imino] acetamide (11.00 g, 40.0 mmol), phosphorus oxychloride (61.95 g, 400.0 mmol) and ethylene dichloride (80 mL) was added into a reaction flask. The mixture was stirred at 80° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((3, 4-dichlorophenyl)methoxy)imino] malononitrile (9.03 g as white solid with yield of 88% (calculated by the 2-cyano-2-[((3, 4-dichlorophenyl)methoxy)imino] acetamide).

$^1$HNMR (600 MHz, CDCl$_3$) δ (ppm): 7.50 (d, 1H), 7.48 (d, 1H), 7.23 (dd, 1H), 5.46 (s, 2H).

Embodiment 2

1) Preparation of 2-cyano-2-[((2-phenylthiazole-4-yl)methoxy)imino] acetamide (compound 60)

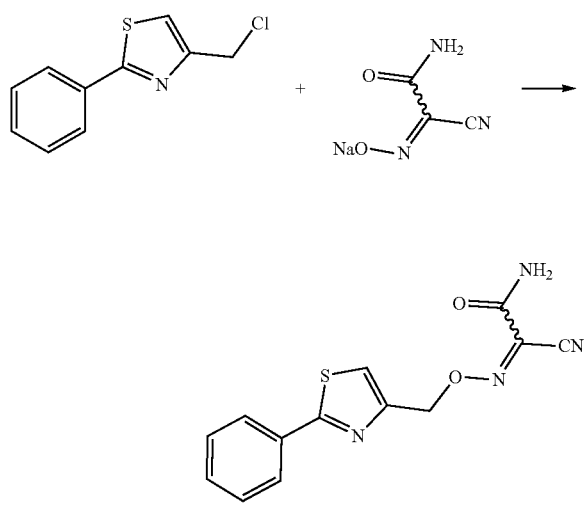

A mixture of 4-(chloromethyl)-2-phenylthiazole (10.59 g, 50.0 mmol), 2-cyano-2-hydroximino acetamide sodium salt (11.37 g, 80.0 mmol), tetrabutylammonium bromide (0.82 g, 2.5 mmol) and acetone (80 mL) was added into a reaction flask. The mixture was stirred at 60° C. for 12 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 60 (11.86 g, analysis by HNMR, isomers Z:E=1:1) as white solid with yield of 82% (calculated by 4-(chloromethyl)-2-phenylthiazole).

$^1$HNMR (600 MHz, CDCl$_3$) δ (ppm): 7.95-7.93 (m, 2H), 7.46-7.45 (m, 3H), 7.36 (s, 1H), 6.52 (s, 1H), 5.68 (s, 1H), 5.61 (s, 2H).

2) Preparation of 2-[((2-phenylthiazole-4-yl)methoxy)imino] malononitrile

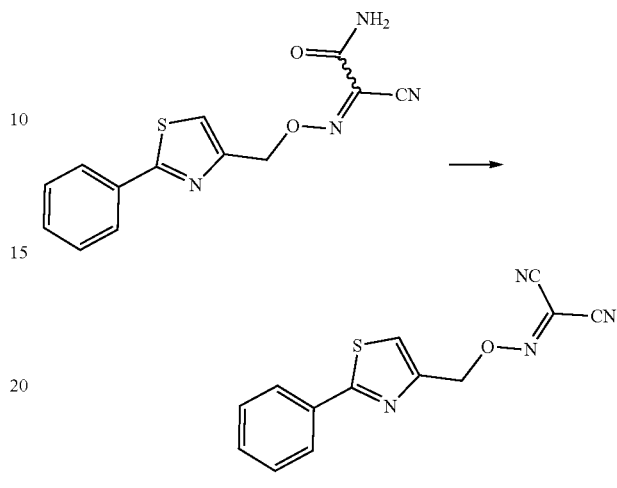

A mixture of 2-cyano-2-[((2-phenylthiazole-4-yl)methoxy)imino] acetamide (11.57 g, 40.0 mmol), phosphorus oxychloride (55.75 g, 360.0 mmol) and trichloromethane (80 mL) was added into a reaction flask. The mixture was stirred at 70° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((2-phenylthiazole-4-yl)methoxy)imino] malononitrile (9.32 g as pale yellow solid with yield of 86% (calculated by the 2-cyano-2-[((2-phenylthiazole-4-yl)methoxy)imino] acetamide).

$^1$HNMR (600 MHz, CDCl$_3$) δ (ppm): 7.95-7.94 (m, 2H), 7.46-7.45 (m, 3H), 7.40 (s, 1H), 5.67 (s, 2H).

Embodiment 3

1) Preparation of 2-cyano-2-[((2-(4-chlorophenyl) thiazol-4-yl)methoxy)imino]acetamide (compound 61)

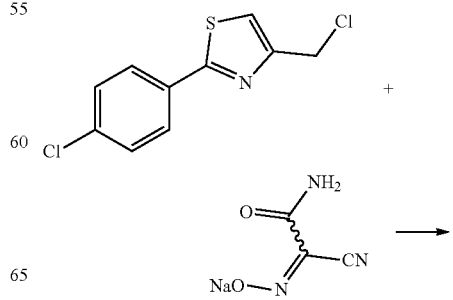

-continued

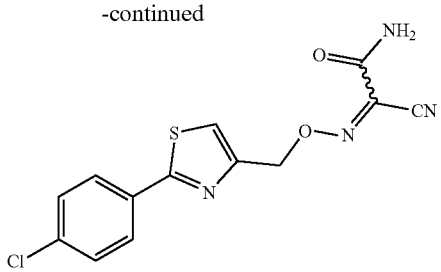

A mixture of 4-(chloromethyl)-2-(4-chlorophenyl)thiazol (12.33 g, 50.0 mmol), 2-cyano-2-hydroximino acetamide sodium salt (11.37 g, 80.0 mmol), triethylbenzylammonium chloride 0.35 g, 1.5 mmol) and butanone (80 mL) was added into a reaction flask. The mixture was stirred at 70° C. for 12 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 61 (13.12 g, analysis by HNMR, isomers Z:E=1: 1) as white solid with yield of 81% (calculated by the 4-(chloromethyl)-2-(4-chlorophenyl)thiazol).

$^1$HNMR (600 MHz, CDCl$_3$) δ (ppm): 7.88 (d, 2H), 7.43 (d, 2H), 7.37 (s, 1H), 6.48 (s, 1H), 5.67 (s, 2H), 5.50 (s, 1H).

2) Preparation of 2-[((2-(4-chlorophenyl)thiazol-4-yl)methoxy)imino]malononitrile

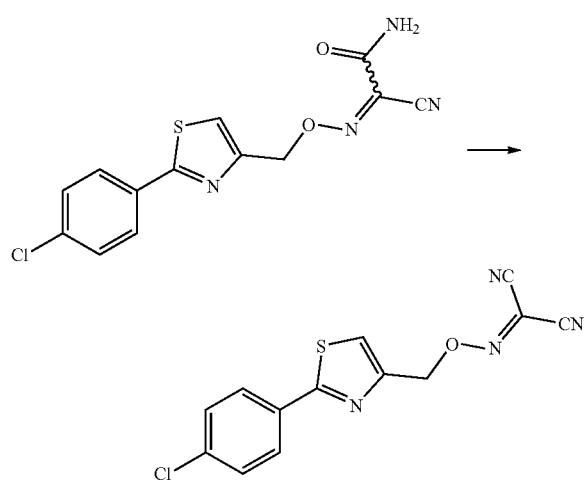

A mixture of 2-cyano-2-[((2-(4-chlorophenyl)thiazol-4-yl)methoxy)imino]acetamide (12.96 g, 40.0 mmol), phosphorus oxychloride (55.75 g, 360.0 mmol) and trichloromethane (80 mL) was added into a reaction flask. The mixture was stirred at 70° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((2-(4-chlorophenyl)thiazol-4-yl) methoxy)imino]malononitrile (10.52 g as pale yellow solid with yield of 86% (calculated by 2-cyano-2-[((2-(4-chlorophenyl)thiazol-4-yl)methoxy)imino] acetamide).

$^1$HNMR (300 MHz, CDCl$_3$) δ (ppm): 7.89 (d, 2H), 7.44 (d, 2H), 7.42 (s, 1H), 5.67 (s, 2H).

Embodiment 4

1) Preparation of 2-cyano-2-[(((4-methoxyphenyl) methoxy)imino] acetamide

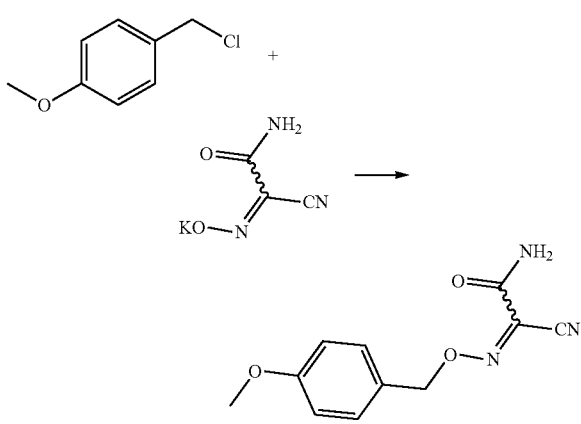

A mixture of 4-methoxybenzyl chloride (7.91 g, 50.0 mmol), 2-cyano-2-hydroximino acetamide potassium salt (14.32 g, 90.0 mmol), sodium iodide (0.76 g, 5.0 mmol) and DMF (40 mL) was added into a reaction flask. The mixture was stirred at 40° C. for 12 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[(((4-methoxyphenyl) methoxy)imino] acetamide (9.66 g, analysis by HNMR, isomers Z:E=1:1) as white solid with yield of 82% (calculated by 4-methoxybenzyl chloride).

$^1$HNMR (600 MHz, CDCl$_3$) δ (ppm): 7.32 (d, 2H), 6.92 (d, 2H), 6.41 (s, 1H), 5.90 (s, 1H), 5.36 (s, 2H), 3.83 (s, 3H).

2) Preparation of 2-[(((4-methoxyphenyl)methoxy)imino] malononitrile

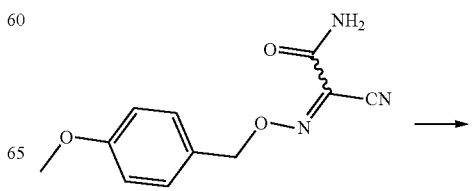

-continued

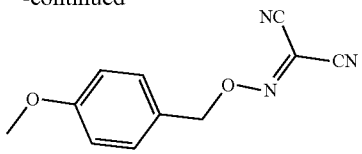

A mixture of 2-cyano-2-[((4-methoxyphenyl)methoxy)imino] acetamide (9.43 g, 40.0 mmol), phosphorus oxychloride (61.95 g, 400.0 mmol) and toluene (80 mL) was added into a reaction flask. The mixture was stirred at 80° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((4-methoxyphenyl)methoxy)imino] malononitrile (7.57 g as colourless oil with yield of 87% (calculated by the 2-cyano-2-[((4-methoxyphenyl)methoxy)imino] acetamide).

$^1$HNMR (300 MHz, CDCl$_3$) δ (ppm): 7.33 (dd, 2H), 6.93 (dd, 2H), 5.46 (s, 2H), 3.83 (s, 3H).

Embodiment 5

1) Preparation of 2-cyano-2-[((6-chloropyridine-3-yl)methoxy)imino] acetamide (compound 29)

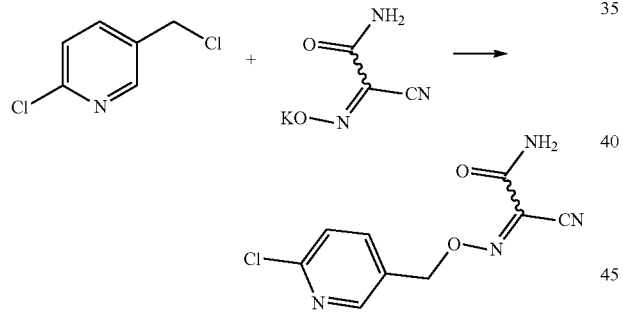

A mixture of 2-chloro-5-chloromethylpyridine (8.19 g, 50.0 mmol), 2-cyano-2-hydroximino acetamide potassium salt (14.32 g, 90.0 mmol), potassium iodide (0.84 g, 5.0 mmol) and DMF (40 mL) was added into a reaction flask. The mixture was stirred at 40° C. for 12 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[((6-chloropyridine-3-yl)methoxy)imino] acetamide (9.88 g, analysis by HNMR, isomers Z:E=1:1) as white solid with yield of 82% (calculated by the 2-chloro-5-chloromethylpyridine).

$^1$HNMR (600 MHz, CDCl$_3$) δ (ppm): 8.44 (s, 1H), 7.72 (d, 2H), 7.42 (d, 2H), 6.34 (s, 1H), 5.56 (s, 1H), 5.43 (s, 2H).

2) Preparation of 2-[((6-chloropyridine-3-yl)methoxy)imino] malononitrile

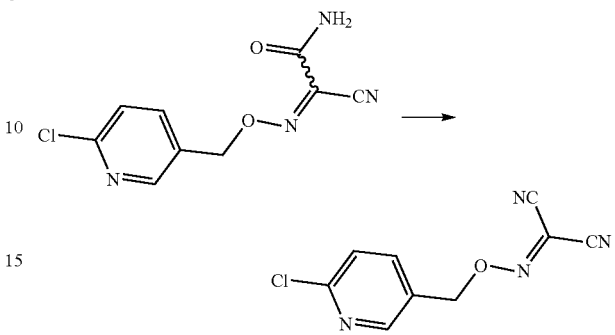

A mixture of 2-cyano-2-[((6-chloropyridine-3-yl)methoxy)imino] acetamide (9.64 g, 40.0 mmol), phosphorus oxychloride (61.95 g, 400.0 mmol) and toluene (80 mL) was added into a reaction flask. The mixture was stirred at 80° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((6-chloropyridine-3-yl)methoxy)imino] malononitrile (7.58 g as pale yellow oil with yield of 85% (calculated by the 2-cyano-2-[((6-chloropyridine-3-yl)methoxy)imino] acetamide).

$^1$HNMR (600 MHz, CDCl$_3$) δ (ppm): 8.45 (s, 1H), 7.71 (d, 1H), 7.43 (d, 1H), 5.52 (s, 2H).

Embodiment 6

1) Preparation of 2-cyano-2-[((2-chlorothiazole-5-yl)methoxy)imino] acetamide (compound 192)

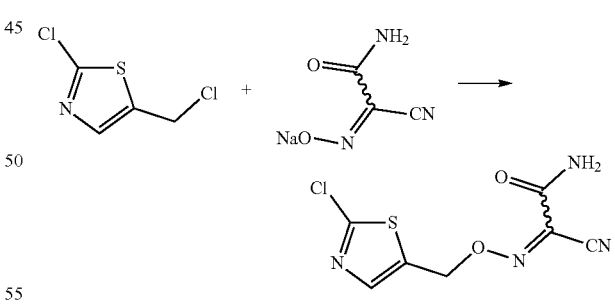

A mixture of 2-chloro-5-chloromethylthiazole (8.49 g, 50.0 mmol), 2-cyano-2-hydroximino acetamide sodium salt (12.80 g, 90.0 mmol), tetrabutylammonium bromide (1.63 g, 5.0 mmol) and acetone (80 mL) was added into a reaction flask. The mixture was stirred at 40° C. for 12 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[((2-chlorothiazole-5-yl)methoxy)imino] acetamide (10.01 g, analysis by HNMR, isomers Z:E=1:1) as white solid with yield of 81% (calculated by the 2-chloro-5-chloromethylthiazole).

$^1$HNMR (600 MHz, CDCl$_3$) δ (ppm): 7.62 (s, 1H), 6.37 (s, 1H), 5.72 (s, 1H), 5.52 (s, 2H).

2) Preparation of 2-[((6-chloropyridine-3-yl)methoxy)imino] malononitrile

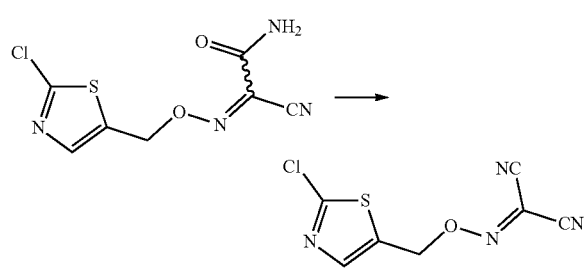

A mixture of 2-cyano-2-[((2-chlorothiazole-5-yl)methoxy)imino] acetamide (9.89 g, 40.0 mmol), phosphorus oxychloride (61.95 g, 400.0 mmol) and trichloromethane (80 mL) was added into a reaction flask. The mixture was stirred at 70° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((2-chlorothiazole-5-yl)methoxy)imino] malononitrile (8.06 g as pale yellow solid with yield of 88% (calculated by the 2-cyano-2-[((2-chlorothiazole-5-yl)methoxy)imino] acetamide).

$^1$HNMR (600 MHz, CDCl$_3$) δ (ppm): 7.65 (s, 1H), 5.62 (s, 2H).

Embodiment 7

1) Preparation of 2-cyano-2-[((quinoline-6-yl)methoxy)imino] acetamide (compound 105)

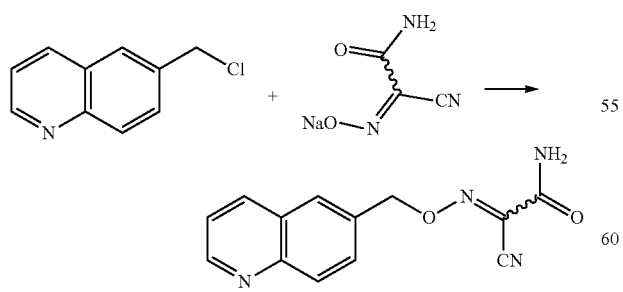

A mixture of 6-chloromethyl)quinoline (8.98 g, 50.0 mmol), 2-cyano-2-hydroximino acetamide sodium salt (12.80 g, 90.0 mmol), tetrabutylammonium bromide (1.63 g, 5.0 mmol) and acetone (80 mL) was added into a reaction flask. The mixture was stirred at 50° C. for 12 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[((quinoline-6-yl)methoxy)imino] acetamide (10.66 g, analysis by HNMR, isomers Z:E=1:1) as yellow solid with yield of 83% (calculated by the 6-chloromethyl)quinoline).

$^1$HNMR (600 MHz, DMSO-d$_6$) δ(ppm): 8.99 (d, 1H), 8.41 (t, 1H), 8.09-8.06 (m, 2H), 8.05 (s, 1H), 7.98 (s, 1H), 7.86 (d, 1H), 7.59-7.57 (m, 1H), 5.68 (s, 2H).

2) Preparation of 2-[((quinoline-6-yl)methoxy)imino] malononitrile

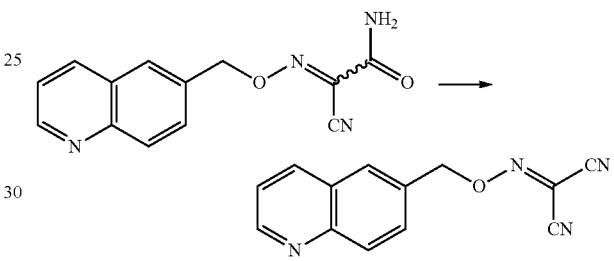

A mixture of 2-cyano-2-[((quinoline-6-yl)methoxy)imino] acetamide (10.27 g, 40.0 mmol), phosphorus oxychloride (61.95 g, 400.0 mmol) and trichloromethane (80 mL) was added into a reaction flask. The mixture was stirred at 70° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((quinoline-6-yl)methoxy)imino] malononitrile (8.40 g as yellow oil with yield of 88% (calculated by the 2-cyano-2-[((quinoline-6-yl)methoxy)imino] acetamide).

HNMR (300 MHz, CDCl$_3$) δ (ppm): 8.94 (dd, 1H), 8.23 (d, 1H), 8.18 (d, 1H), 7.87 (s, 1H), 7.72 (dd, 1H), 7.52-7.48 (m, 1H), 5.72 (s, 2H).

Embodiment 8

1) Preparation of 2-cyano-2-[((3-bromophenyl)methoxy)imino] acetamide

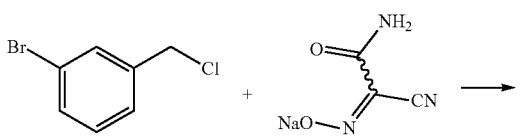

-continued

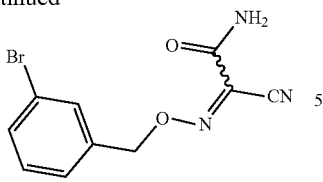

A mixture of 3-bromobenzyl chloride (10.37 g, 50.0 mmol), 2-cyano-2-hydroximino acetamide sodium salt (12.80 g, 90.0 mmol), tetrabutylammonium bromide (1.63 g, 5.0 mmol) and acetone (80 mL) was added into a reaction flask. The mixture was stirred at 60° C. for 10 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[((3-bromophenyl)methoxy)imino] acetamide (11.83 g, analysis by HNMR, isomers Z:E=1:1) as white solid with yield of 83% (calculated by the 3-bromobenzyl chloride).

$^1$HNMR (600 MHz, CDCl$_3$) δ (ppm): 7.54-7.52 (m, 2H), 7.32-7.29 (m, 2H), 6.39 (s, 1H), 5.92 (s, 1H), 5.39 (s, 2H).

2) Preparation of 2-[((3-bromophenyl)methoxy)imino] malononitrile

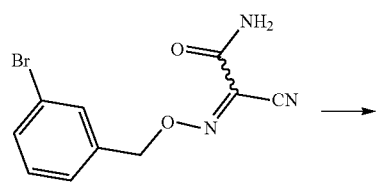

A mixture of 2-cyano-2-[((3-bromophenyl)methoxy) imino] acetamide (11.40 g, 40.0 mmol), thionyl chloride (48.07 g, 400.0 mmol) and toluene (80 mL) was added into a reaction flask. The mixture was stirred at 80° C. for 8 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((3-bromophenyl)methoxy) imino] malononitrile (9.07 g as yellow oil with yield of 85% (calculated by the 2-cyano-2-[((3-bromophenyl)methoxy) imino] acetamide).

$^1$HNMR (300 MHz, CDCl$_3$) δ (ppm): 7.57-7.53 (m, 2H), 7.33-7.30 (m, 2H), 5.47 (s, 2H).

Embodiment 9

1) Preparation of 2-cyano-2-[((4-cyanophenyl) methoxy)imino] acetamide

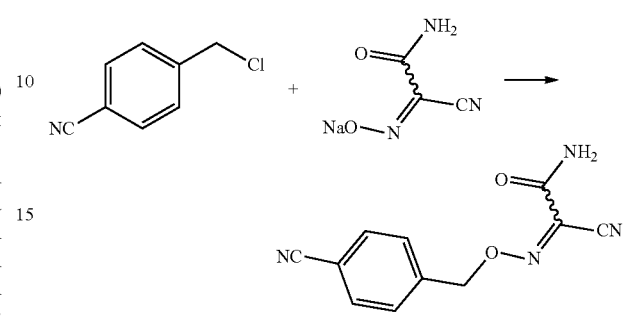

A mixture of 4-(chloromethyl)benzonitrile (7.66 g, 50.0 mmol), 2-cyano-2-hydroximino acetamide sodium salt (12.80 g, 90.0 mmol), tetrabutylammonium bromide (1.63 g, 5.0 mmol) and butanone (80 mL) was added into a reaction flask. The mixture was stirred at 80° C. for 10 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[((4-cyanophenyl)methoxy)imino] acetamide (9.68 g, analysis by HNMR, isomers Z:E=1:1) as white solid with yield of 84% (calculated by the 4-(chloromethyl) benzonitrile).

$^1$HNMR (600 MHz, CDCl$_3$) δ (ppm): 7.72 (d, 2H), 7.49 (d, 2H), 6.33 (s, 1H), 5.49 (s, 2H), 5.48 (s, 1H).

2) Preparation of 2-[((4-cyanophenyl)methoxy)imino] malononitrile

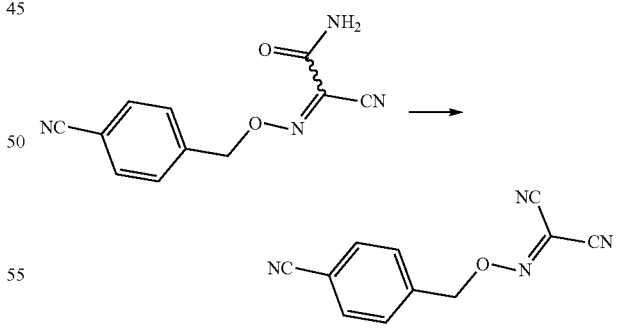

A mixture of 2-cyano-2-[((4-cyanophenyl)methoxy) imino] acetamide (9.22 g, 40.0 mmol), phosphorus oxychloride (61.95 g, 400.0 mmol) and acetonitrile (80 mL) was added into a reaction flask. The mixture was stirred at 70° C. for 10 h and monitored by Thin-Layer Chromatography until the reaction was over. After completion of the reaction, the reaction mixture was cooled to room temperature and poured into ice water slowly. The mixture was extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-[((4-cyanophenyl)methoxy)imino] malononitrile (7.14 g as white solid with yield of 84% (calculated by the 2-cyano-2-[((4-cyanophenyl)methoxy)imino]acetamide).

¹HNMR (300 MHz, CDCl₃) δ (ppm): 7.74 (d, 2H), 7.50 (d, 2H), 5.57 (s, 2H).

Embodiment 10

1) Preparation of 2-cyano-2-[((2-methyl-4-phenylphenyl)methoxy)imino]acetamide

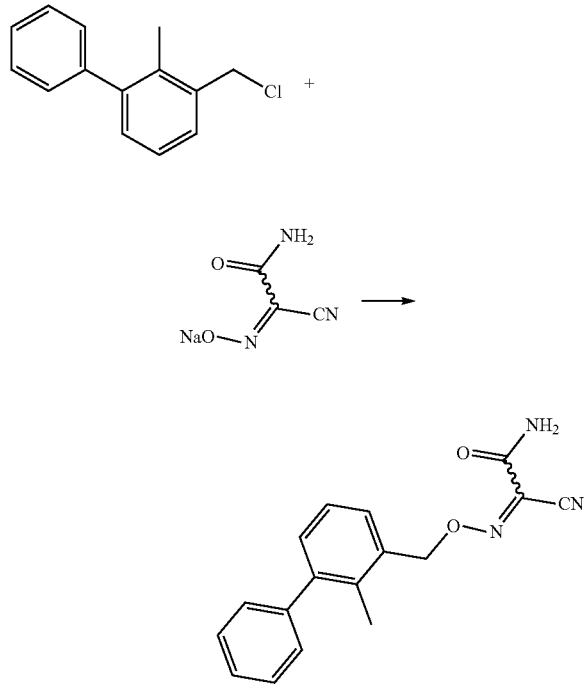

A mixture of 2-methyl-3-phenylbenzyl chloride (10.95 g, 50.0 mmol), 2-cyano-2-hydroximino acetamide sodium salt (12.80 g, 90.0 mmol), tetrabutylammonium bromide (1.63 g, 5.0 mmol) and acetonitrile (80 mL) was added into a reaction flask. The mixture was stirred at 60° C. for 10 h and monitored by Thin-Layer Chromatography until the reaction was over. After completion of the reaction, the reaction mixture was cooled to room temperature and extracted with ethyl acetate (100 mL) and water (50 mL). Then the organic phase was washed with saturated brine, dried over anhydrous magnesium sulfate, filtered and then concentrated under reduced pressure. the residue was purified by column chromatography on silica gel to obtain the compound 2-cyano-2-[((2-methyl-4-phenylphenyl)methoxy)imino] acetamide (12.00 g, analysis by HNMR, isomers Z:E=1:1) as white solid with yield of 81% (calculated by the 4-(chloromethyl)benzonitrile).

¹HNMR (600 MHz, CDCl₃) δ(ppm): 7.44-7.41 (m, 2H), 7.38-7.35 (m, 1H), 7.33-7.32 (m, 1H), 7.30-7.27 (m, 4H), 6.42 (s, 1H), 5.85 (s, 1H), 5.54 (s, 2H), 2.27 (s, 3H).

2) Preparation of 2-[((4-cyanophenyl)methoxy)imino] malononitrile

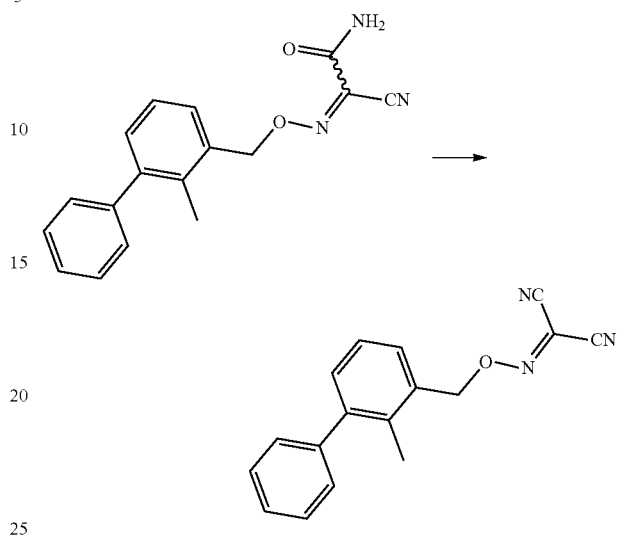

A mixture of 2-cyano-2-[((2-methyl-4-phenylphenyl)methoxy)imino] acetamide (11.85 g, 40.0 mmol), phosphorus oxychloride (61.95 g, 400.0 mmol) and ethylene dichloride (80 mL) was added into a reaction flask. The mixture was stirred at 70° C. for 10 h and monitored by Thin-Layer Chromatography until the reaction was over. After completion of the reaction, the reaction mixture was cooled to room temperature and poured into ice water slowly. Then the organic phase was washed with saturated brine, dried over anhydrous magnesium sulfate, filtered and then concentrated under reduced pressure. the residue was purified by column chromatography on silica gel to obtain the compound 2-[((2-methyl-4-phenylphenyl)methoxy)imino] malononitrile (9.57 g as yellow oil with yield of 86% (calculated by the 2-cyano-2-[((2-methyl-4-phenylphenyl)methoxy)imino] acetamide).

¹HNMR (300 MHz, CDCl₃) δ(ppm): 7.44-7.42 (m, 2H), 7.38-7.36 (m, 1H), 7.33-7.32 (m, 2H), 7.30-7.27 (m, 3H), 5.65 (s, 2H), 2.27 (s, 3H).

Embodiment 11

Differences between the embodiment 11 and the embodiment 2 were as follows: the molar ratio of the first raw material to the second raw material to the catalyst was 1 to 1.6 to 0.03; and the yield of the compound 60 was 75%.

Embodiment 12

Differences between the embodiment 12 and the embodiment 2 were as follows: in the preparation process of the intermediate compound, the reaction temperature was 100° C.; and the yield of the compound 60 was 70%.

Embodiment 13

Differences between the embodiment 13 and the embodiment 9 were as follows: in the dehydration reaction process, the molar ratio of the intermediate compound to the dehydrating agent was 1 to 0.5.

The yield of the 2-[((4-cyanophenyl)methoxy)imino] malononitrile was 65%.

Embodiment 14

Differences between the embodiment 14 and the embodiment 2 were as follows: the first raw material was 1-methyl-1-hydro-2-pyrrolylbenzyl chloride; the yield of 2-cyano-2-[((1-methyl-1-hydro-pyrrolyl-2-yl)methoxy)imino] acetamide, as the intermediate, was 76%; and the yield of the 2-[((1-methyl-1-hydro-pyrrolyl-2-yl)methoxy)imino] malononitrile was 72%.

Embodiment 15

Differences between the embodiment 15 and the embodiment 2 were as follows: the first raw material was 1-methyl-1-hydro-5-pyrazolylbenzyl chloride; the yield of 2-cyano-2-[((1-methyl-1-hydro-pyrazolyl-5-yl)methoxy)imino] acetamide, as the intermediate, was 73%; and the yield of preparing the 2-[((1-methyl-1-hydro-pyrazolyl-5-yl)methoxy)imino] malononitrile was 74%.

From the above description, it could be seen that the present disclosure could realize the following technological effects:

Known from the background art, the yield of the malononitrile oxime ether compound represented by formula I was lower than 60% generally, comparison from the embodiment 1 to the embodiment 10 showed that the yields of the malononitrile oxime ether compound represented by formula (VII) were all larger than 80%, and thus, by the preparation method provided by the present application, the yield of the malononitrile oxime ether compound might be greatly increased.

Comparison among the embodiment 2, the embodiment 11 and the embodiment 12 showed that increase in yield of the intermediate compound was facilitated if the molar ratio of the first raw material to the second raw material to the catalyst was limited in a preferred range of the present application in the preparation process of the intermediate compound.

Comparison between the embodiment 9 and the embodiment 13 showed that increase in yield of the intermediate compound was facilitated if the molar ratio of the intermediate compound to the dehydrating agent was limited in a preferred range of the present application in the dehydration reaction process.

Comparison among the embodiment 2, the embodiment 14 and the embodiment 15 showed that increase in yield of the malononitrile oxime ether compound was facilitated by preferably selecting the substituent in the structure represented by the formula (IV).

What stated above are merely preferred examples of the present disclosure but are not used to limit the present disclosure, and various modifications and variations can be made in the present disclosure to those skilled in the art. Any modifications, equivalent substitutions, improvements and the like within the spirit and principles of the present disclosure are intended to be embraced by the protection range of the present disclosure.

What is claimed is:

1. A preparation method for a malononitrile oxime ether compound represented by a formula (VI),

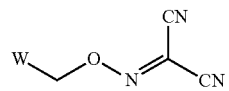

wherein W is selected from aryl groups or heteroaryl groups,
the preparation method comprises the following steps:
enabling a first raw material of formula (IV) to be reacted with a second raw material of formula (V) in the presence of a first solvent and a catalyst to obtain an intermediate compound of formula (VI), wherein the intermediate compound of formula (VI) is synthesized by a synthetic route as follows:

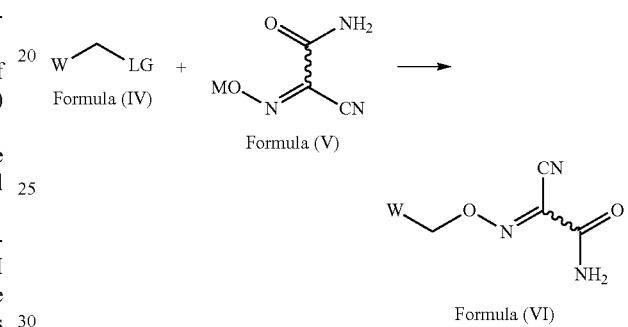

wherein LG represents leaving groups, M is selected from monovalent cations, W is selected from aryl groups or the heteroaryl groups, "〰〰" represents a chemical bond, and a configuration of double bonds may be (Z)- or (E)-;
and performing a dehydration reaction with the intermediate compound represented by the formula (VI) and a dehydrating agent in the presence of a second solvent to obtain the malononitrile oxime ether compound represented by formula (VII), wherein the malononitrile oxime ether compound represented by formula (VII) is synthesized by a synthetic route as follows:

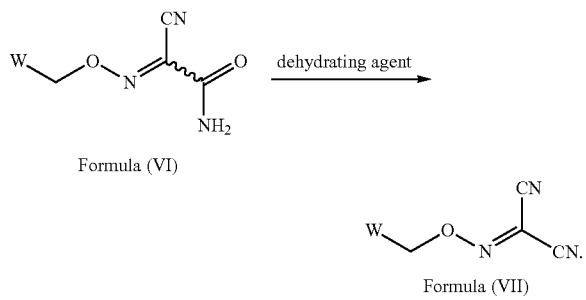

2. The preparation method according to claim 1, wherein in the dehydration reaction process, a molar ratio of the intermediate compound of formula (VI) and the dehydrating agent is 1 to (1-20).

3. The preparation method according to claim 1, wherein the dehydrating agent is one or more selected from a group consisting of acetic anhydride, bistrichloromethyl carbonate, thionyl chloride, phosphorus oxychloride and phosphorus pentoxide; and the second solvent is one or more selected from a group consisting of halogenated alkane compounds, aromatic hydrocarbon compounds, nitrile compounds and DMF.

4. The preparation method according to claim 1, wherein a reaction temperature of the dehydration reaction is 0-150° C., and a reaction time of the dehydration reaction is 0.5-48 h.

5. The preparation method according to claim 1, wherein the LG is a halogen.

6. The preparation method according to claim 1, wherein the M is selected from $Na^+$, $K^+$, $C_S^+$, $Ag^+$ or $NH_4^+$.

7. The preparation method according to claim 1, wherein the catalyst is one or more selected from a group consisting of NaI, KI, tetrabutylammonium bromide and benzyltriethylammoniumchloride; and the first solvent is one or more selected from a group consisting of nitrile compounds, ketone compounds, DMF, DMSO, 1, 3-dimethyl-2-imidazolidinone and N-methyl-2-pyrrolidone.

8. The preparation method according to claim 1, wherein in the preparation process of the intermediate compound of formula (VI), a molar ratio of the first raw material of formula (IV), the second raw material of formula (V) and the catalyst is 1 to (1-5) to (0.05-0.5).

9. The preparation method according to claim 1, wherein a reaction temperature of the preparation process of the intermediate compound is 0-150° C., and a reaction time of the preparation process of the intermediate compound is 0.5-48 h.

10. The preparation method according to claim 1, wherein the W is selected from any one of $W^1$-$W^{84}$;

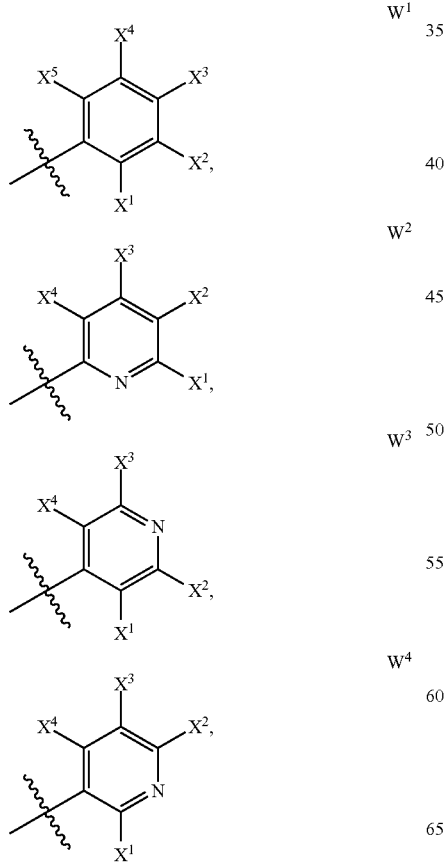

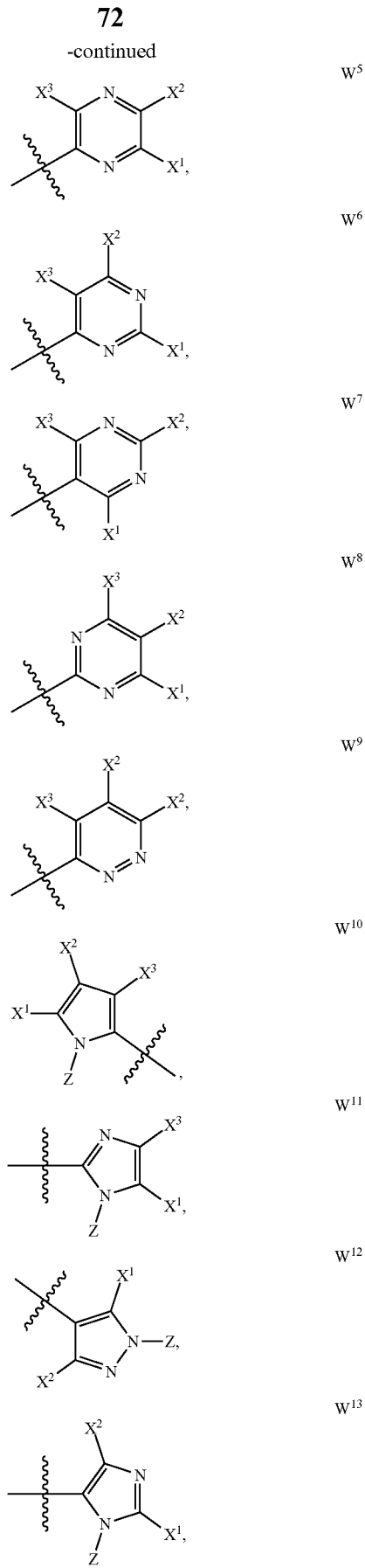

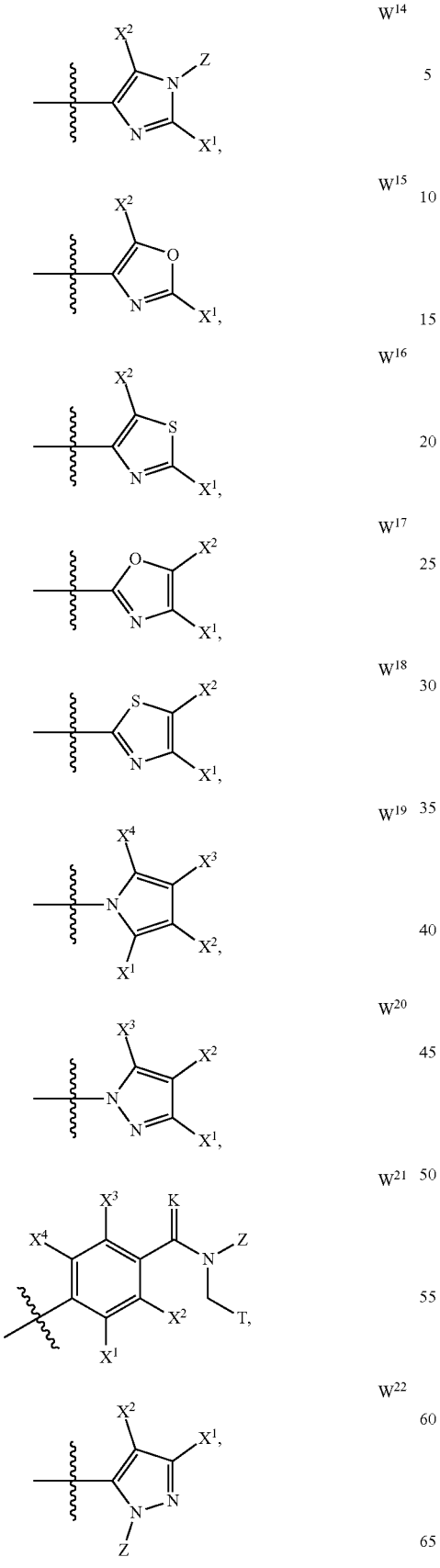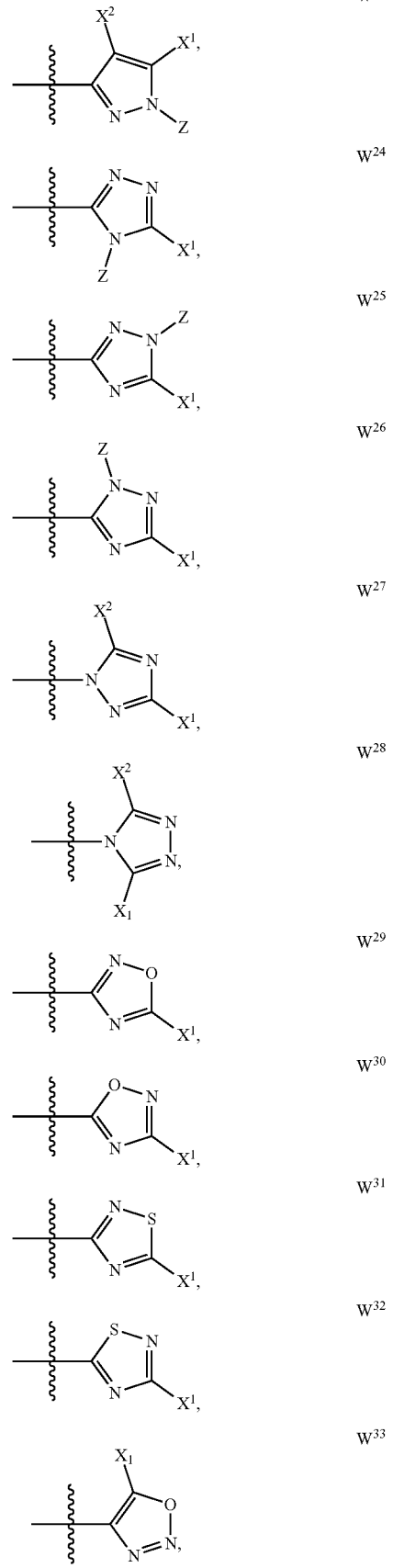

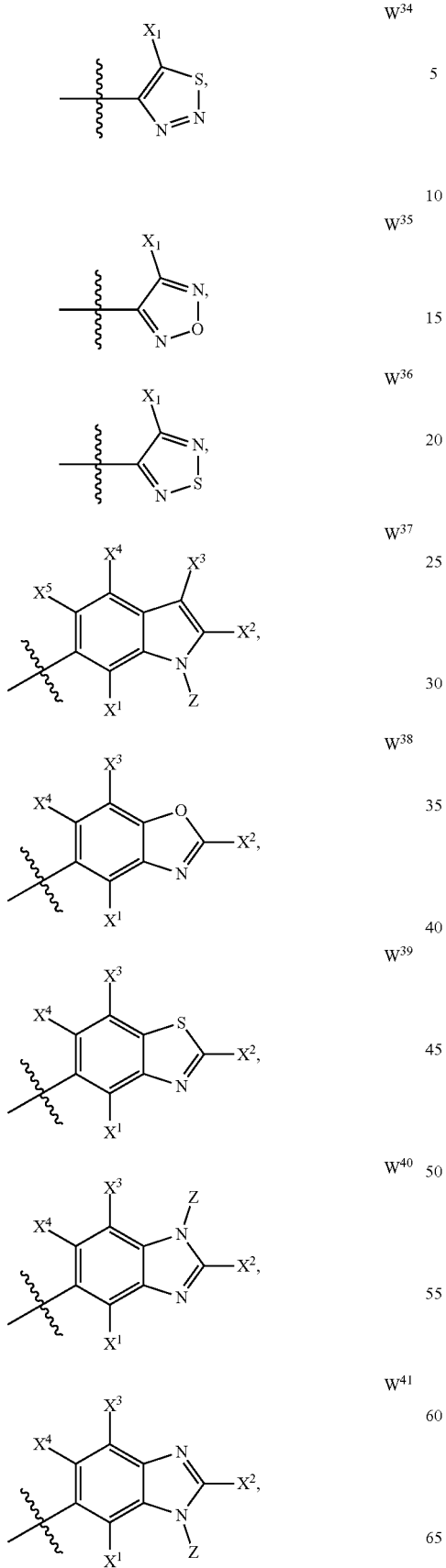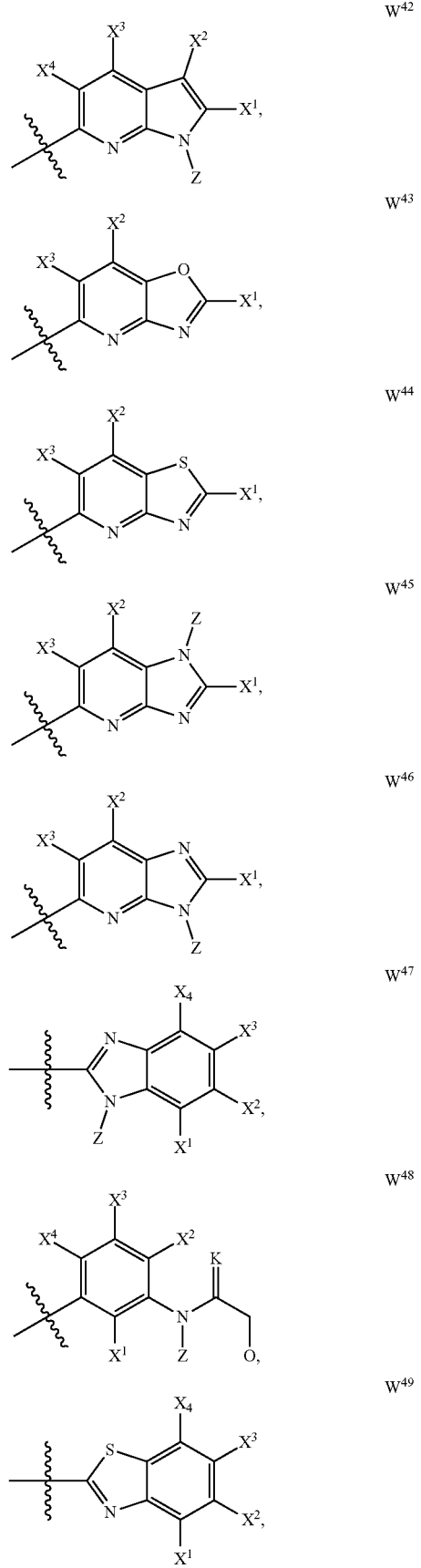

-continued
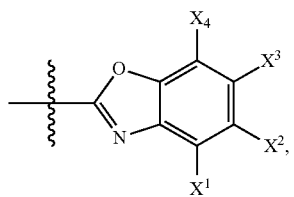 W50
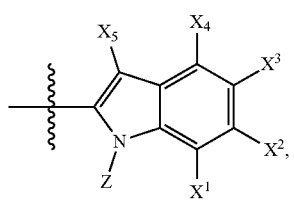 W51
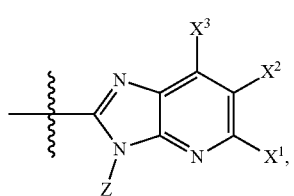 W52
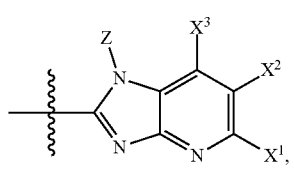 W53
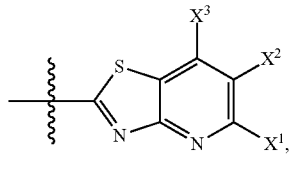 W54
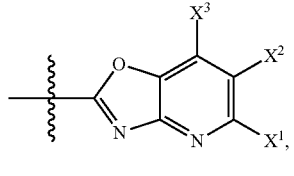 W55
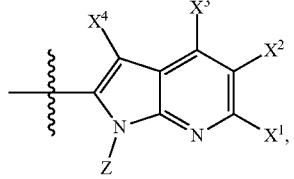 W56
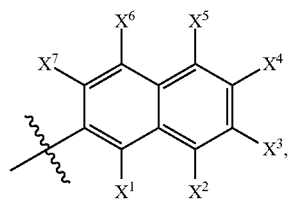 W57
-continued
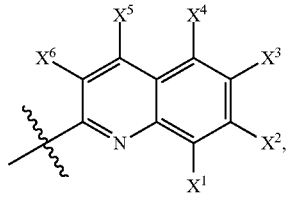 W58
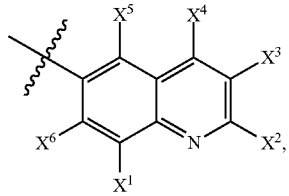 W59
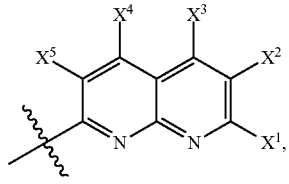 W60
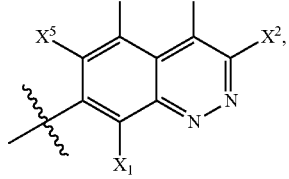 W61
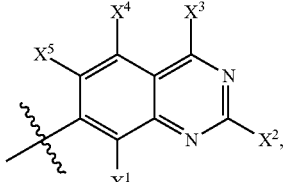 W62
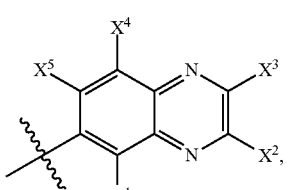 W63
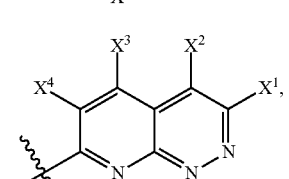 W64
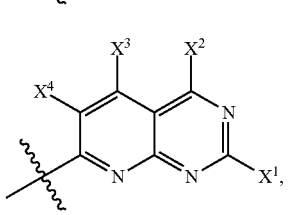 W65

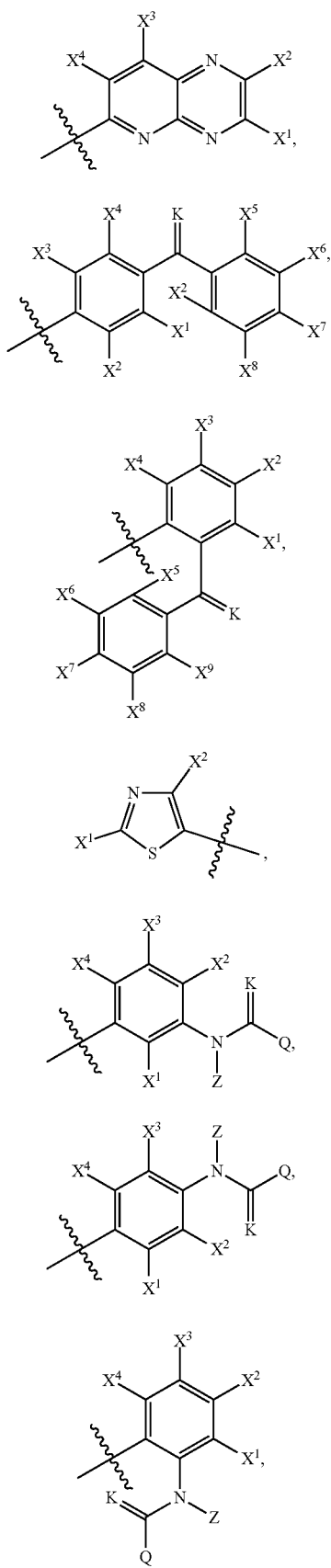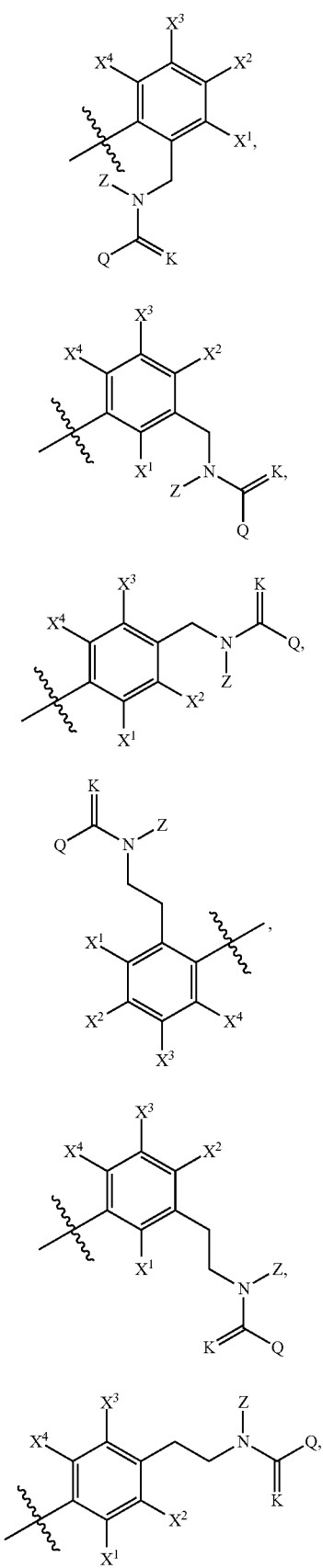

-continued

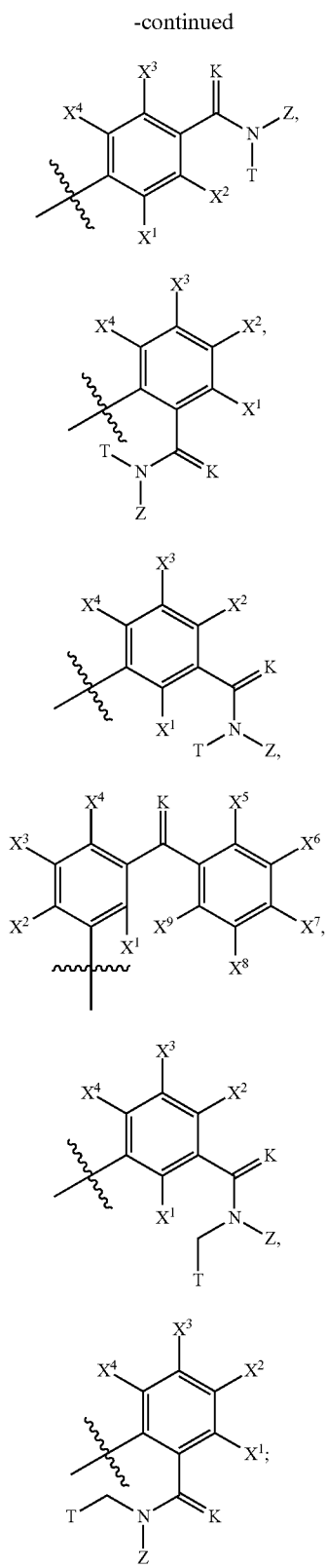

W<sup>79</sup>

W<sup>80</sup>

W<sup>81</sup>

W<sup>82</sup>

W<sup>83</sup>

W<sup>84</sup> wherein $X^1$, $X^2$, $X^3$, $X^4$, $X^5$, $X^6$, $X^7$, $X^8$ and $X^9$ are independently selected from hydrogen, halogens, cyano groups, nitro groups, —$SF_5$, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, $C_1$-$C_8$ alkoxy groups, $C_1$-$C_8$ alkyl groups, —OR, —C(=O)OR$^3$, —N(R$^4$)S(=O)$_2$R$^5$, —S(=O)$_2$NR$^3$R$^5$, —N(R$^4$)C(=O)OR$^3$, —CR$^4$=NOR$^3$, —CH$_2$ON=C(CN)$_2$, —C(=O)SR$^3$, —C(=S)OR$^3$, —C(=S)SR$^3$, —CR$^4$=NR$^5$, —CR$^4$=N—NR$^3$R$^5$, —OSiR$^4$R$^5$R$^6$, —OC(=O)R$^4$, —OC(=O)OR$^3$, —OC(=O)NR$^3$R$^4$, —OC(=S)NR$^3$R$^4$, —NR$^3$R$^4$, —N(R$^4$)C(=O)NR$^3$R$^5$, —N(R$^4$)C(=S)NR$^3$R$^5$, —N=CR$^4$R$^5$, —N=C—NR$^3$R$^4$, —N(R$^4$)C(=NR$^5$)NR$^3$R$^6$, —N(R$^4$)OR$^3$, —N(R$^4$)NR$^3$R$^5$, —N=NR$^4$, —N(R$^4$)S(=O)R$^5$, —N(R$^4$)S(=O)$_2$OR$^3$, —N(R$^4$)S(=O)OR$^3$, —N(R$^4$)S(=O)NR$^3$R$^5$, —N(R$^4$)S(=O)$_2$NR$^3$R$^5$, NR$^4$C(=O)R$^5$, —SR$^3$, —S(=O)$_2$R$^4$, —S(=O)R$^4$, —S(=O)OR$^3$, —S(=O)NR$^3$R$^4$, —S(=O)$_2$OR$^3$, —S(=O)NR$^3$R$^4$, —SiR$^3$R$^4$R$^5$, a group G$^1$ or a group G$^1$ optionally substituted with a substitutent J$^1$, wherein the group G$^1$ is selected from phenyl groups, pyridyl groups, pyrazolyl groups, thiazolyl groups, isothiazolyl groups or thiadiazolyl groups, and the substituent J$^1$ is selected from halogens, cyano groups, nitro groups, $C_1$-$C_8$ alkyl groups, $C_1$-$C_8$ haloalkyl groups, $C_1$-$C_8$ alkoxy groups, $C_1$-$C_8$ haloalkoxy groups, $C_1$-$C_8$ alkylthio groups or $C_1$-$C_8$ haloalkylthio groups;

Z is selected from hydrogen, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, aryl groups, $C_1$-$C_8$ alkyl groups substituted with aryl groups, $C_1$-$C_8$ alkyl groups substituted with $C_1$-$C_8$ alkoxy groups, —C(=O)R$^3$ or —C(=O)OR$^3$;

K is selected from oxygen, sulfur, NR$^3$, N—OR$^4$ or N—NR$^3$R$^4$;

R$^3$ is selected from hydrogen, $C_1$-$C_8$ alkyl groups, $C_1$-$C_8$ haloalkyl groups, $C_3$-$C_6$ cycloalkyl groups, $C_1$-$C_8$ alkoxycarbonyl groups, $C_2$-$C_8$ alkenyl groups, $C_2$-$C_8$ haloalkenyl groups, $C_2$-$C_8$ alkynyl groups, $C_2$-$C_8$ haloalkynyl groups, a group G$^2$ or a group G$^2$ optionally substituted with a substituent J$^2$, wherein the group G$^2$ is selected from phenyl groups, pyridyl groups, pyrazolyl groups, thiazolyl groups, isothiazolyl groups or thiadiazolyl groups, and the substituent J$^2$ is selected from halogens, cyano groups, nitro groups, hydroxyl groups, thiol groups, amino groups, —CONH$_2$, —COOH, —CHO, $C_1$-$C_4$ alkyl groups, $C_1$-$C_4$ haloalkyl groups, $C_1$-$C_3$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, amino groups substituted with $C_1$-$C_3$ alkyl, amino groups substituted with $C_1$-$C_3$ dialkyl, amino groups substituted with $C_3$-$C_6$ cycloalkyl, $C_1$-$C_3$ alkoxycarbonyl groups, $C_1$-$C_3$ alkylsulphonyl groups, aminocarbonyl groups substituted with $C_1$-$C_3$ alkyl or sulfonamide groups substituted with $C_1$-$C_3$ alkyl;

R$^4$, R$^5$ and R$^6$ are independently selected from hydrogen, $C_1$-$C_8$ alkyl groups, $C_1$-$C_8$ haloalkyl groups, $C_3$-$C_6$ cycloalkyl groups, $C_1$-$C_8$ alkoxy groups, $C_1$-$C_8$ haloalkoxy groups, $C_1$-$C_8$ alkoxycarbonyl groups, $C_2$-$C_8$ alkenyl groups, $C_2$-$C_8$ haloalkenyl groups, $C_2$-$C_8$ alkynyl groups, $C_2$-$C_8$ haloalkynyl groups, a group G$^3$ or a group G$^3$ optionally substituted with a substituent J$^3$, wherein the group G$^3$ is selected from phenyl groups, pyridyl groups, pyrazolyl groups, thiazolyl groups, isothiazolyl groups or thiadiazolyl groups, and the substituent J is selected from halogens, cyano groups, nitro groups, hydroxyl groups, thiol groups, amino groups, —CONH$_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, $C_1$-$C_3$ alkylamino groups, $C_1$-$C_3$ dialkylamino groups, $C_3$-$C_6$ cycloalkylamino groups, $C_1$-$C_3$ alkoxycarbonyl groups, $C_1$-$C_3$ alkylsulphonyl groups, $C_1$-$C_3$ alkylaminocarbonyl groups or $C_1$-$C_3$ alkylaminosulfonyl groups;

Q is selected from a group $G^4$ or a group $G^4$ optionally substituted with a substituent $J^4$, the group $G^4$ is selected from phenyl groups, pyridyl groups, pyrazolyl groups, thiazolyl groups, isothiazolyl groups or thiadiazolyl groups, and the substituent $J^4$ is selected from halogens, cyano groups, nitro groups, hydroxyl groups, thiol groups, amino groups, —$CONH_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_4$ alkylthio groups, $C_1$-$C_3$ haloalkylthio groups, $C_1$-$C_3$ alkylamino groups, $C_1$-$C_3$ dialkylamino groups, $C_3$-$C_6$ cycloalkylamino groups, $C_1$-$C_3$ alkoxycarbonyl groups, $C_1$-$C_3$ alkylsulphonyl groups, $C_1$-$C_3$ alkylaminocarbonyl groups or $C_1$-$C_3$ alkylaminosulfonyl groups; and T is selected from cyano groups, $C_1$-$C_8$ alkyl groups, $C_1$-$C_8$ haloalkyl groups, $C_3$-$C_6$ cycloalkyl groups, $C_2$-$C_8$ alkenyl groups, $C_2$-$C_8$ haloalkenyl groups, $C_2$-$C_8$ alkynyl groups, $C_2$-$C_8$ haloalkynyl groups, a group $G^5$ or a group $G^5$ optionally substituted with a substituent J, wherein the group $G^5$ is selected from phenyl groups, pyridyl groups, pyrazolyl groups, thiazolyl groups, isothiazolyl groups or thiadiazolyl groups, and the substituent $J^5$ is selected from halogens, cyano groups, nitro groups, hydroxyl groups, thiol groups, amino groups, —$CONH_2$, —COOH, —CHO, $C_1$-$C_4$ alkyl groups, $C_1$-$C_4$ haloalkyl groups, $C_3$-$C_6$ cycloalkyl groups, $C_1$-$C_3$ alkoxy groups, $C_1$-$C_3$ haloalkoxy groups, $C_1$-$C_3$ alkylthio groups, $C_1$-$C_3$ haloalkylthio groups, $C_1$-$C_3$ alkylamino groups, $C_1$-$C_3$ dialkylamino groups, $C_3$-$C_6$ cycloalkylamino groups, $C_1$-$C_3$ alkoxycarbonyl groups, $C_1$-$C_3$ alkylsulphonyl groups, $C_1$-$C_3$ alkylaminocarbonyl groups or $C_1$-$C_3$ alkylaminosulfonyl groups, but the W is not selected from the unsubstituted phenyl groups.

11. The preparation method according to claim 10, wherein the W is selected from $W^1$, $W^2$, $W^3$, $W^4$, $W^{12}$, $W^{16}$, $W^{18}$, $W^{21}$, $W^{48}$, $W^{58}$, $W^{59}$, $W^{67}$, $W^{68}$, $W^{69}$, $W^{70}$, $W^{71}$, $W^{72}$, $W^{74}$, $W^{79}$, $W^{80}$, $W^{81}$, $W^{82}$ or $W^{83}$;

the $X^1$, the $X^2$, the $X^3$, the $X^4$, the $X^5$, the $X^6$, the $X^7$, the $X^8$ and the $X^9$ are independently selected from hydrogen, fluorine, chlorine, bromine, cyano groups, nitro groups, methyl groups, ethyl groups, isopropyl groups, chloromethyl groups, bromomethyl groups, difluoromethyl groups, trifluoromethyl groups, heptafluoroisopropyl groups, —$OR^3$, —C(=O)$OR^3$, —N($R^4$)S(=O)$_2R^5$, —S(=O)$_2NR^3R^4$, —N($R^4$)C(=O)$OR^3$, —$CR^4$=$NOR^3$, —$CH_2ON$=C(CN)$_2$, $NR^4C$(=O)$R^5$, the group $G^1$ or a group $G^1$ optionally substituted with a substituent $J^1$, wherein the group $G^1$ is selected from phenyl groups or pyridyl groups, and the substituent $J^1$ is selected from halogens, cyano groups, nitro groups, trifluoromethyl groups, heptafluoropropyl groups, heptafluoroisopropyl groups, methoxy groups or trifluoromethoxy groups;

the Z is selected from hydrogen, methyl groups or benzyl groups;

the K is selected from oxygen;

the $R^3$ is selected from hydrogen, methyl groups, ethyl groups, propyl groups, isopropyl groups, cyclopropyl groups, difluoromethyl groups, trifluoromethyl groups, heptafluoropropyl groups, heptafluoroisopropyl groups, methoxycarbonyl groups, the group $G^2$ or the group $G^2$ optionally substituted with the substituent $J^2$, wherein the group $G^2$ is selected from phenyl groups and pyridyl groups, and the substituent $J^2$ is selected from halogens, cyano groups, nitro groups or trifluoromethyl groups;

the $R^4$ and the $R^5$ are independently selected from hydrogen, methyl groups, ethyl groups, propyl groups, isopropyl groups, cyclopropyl groups, difluoromethyl groups, trifluoromethyl groups, heptafluoropropyl groups, heptafluoroisopropyl groups, methoxy groups, trifluoromethoxy groups, methoxycarbonyl groups, the group $G^3$ or the group $G^3$ optionally substituted with the substituent $J^3$, wherein the group $G^3$ is selected from phenyl groups and pyridyl groups, and the substituent $J^3$ is selected from halogens, cyano groups, nitro groups, methyl groups, ethyl groups, propyl groups, chloromethyl groups, bromomethyl groups, trifluoromethyl groups, heptafluoroisopropyl groups, methoxy groups or trifluoromethoxy groups;

the Q is selected from $Q^1$, $Q^2$, $Q^3$, $Q^4$, $Q^5$, $Q^6$, $Q^7$, $Q^8$, $Q^9$, $Q^{10}$, phenyl groups, pyridyl groups or the group $G^4$ optionally substituted with the substituent $J^4$, wherein the group $G^4$ is selected from phenyl groups or pyridyl groups, and the substituent $J^4$ is selected from halogens, cyano groups, nitro groups, hydroxyl groups, thiol groups, amino groups, chloromethyl groups, bromomethyl groups, difluoromethyl groups, trifluoromethyl groups, heptafluoroisopropyl groups, methoxy groups, ethoxy groups, propoxy groups, isopropoxy groups, trifluoromethoxy groups, methylthio groups, ethylthio groups, trifluoromethylthio groups and trifluoroethylthio groups, and $Q^1$-$Q^{10}$ are as follows:

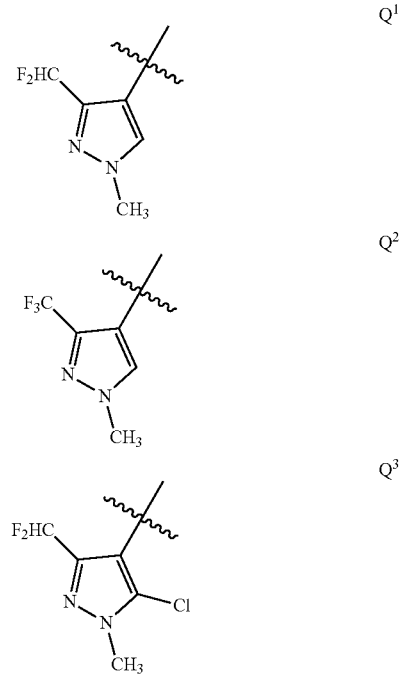

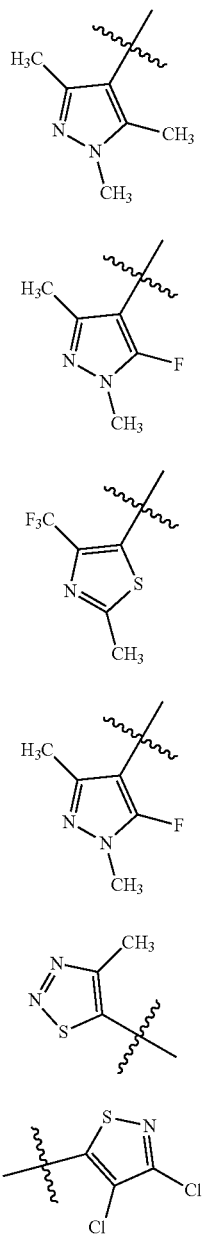

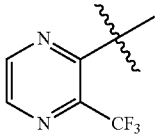

and the T is selected from cyano groups, methyl groups, ethyl groups, propyl groups, isopropyl groups, cyclopropyl groups, trifluoroethyl groups, difluoroethyl groups, cyclopropyl groups, cyclobutyl groups, cyclopentyl groups, cyclohexyl groups, the group $G^5$ or the group $G^5$ optionally substituted with the substituent $J^5$, wherein the group G5 is selected from phenyl groups and pyridyl groups, and the substitutent $J^5$ is selected from halogens, cyano groups, nitro groups, methyl groups, ethyl groups, propyl groups, isopropyl groups, chloromethyl groups, bromomethyl groups, trifluoromethyl groups, heptafluoroisopropyl groups, cyclopropyl groups, cyclobutyl groups, cyclopentyl groups, cyclohexyl groups, methoxy groups, ethoxy groups, propoxy groups, isopropoxy groups, trifluoromethoxy groups, methylthio groups, ethylthio groups, trifluoromethylthio groups or trifluoroethylthio groups.

12. The preparation method according to claim 11, wherein the W is selected from $W^1$, $W^2$, $W^3$, $W^4$, $W^{16}$, $W^{18}$, $W^{59}$ or $W^{69}$.

13. The preparation method according to claim 2, wherein the dehydrating agent is one or more selected from a group consisting of acetic anhydride, bistrichloromethyl carbonate, thionyl chloride, phosphorus oxychloride and phosphorus pentoxide; and the second solvent is one or more selected from a group consisting of halogenated alkane compounds, aromatic hydrocarbon compounds, nitrile compounds and DMF.

14. The preparation method according to claim 13, wherein a reaction temperature of the dehydration reaction is 0-150° C., and a reaction time is 0.5-48 h.

15. The preparation method according to claim 14, wherein in the preparation process of the intermediate compound of formula (VI), a molar ratio of the first raw material of formula (IV), the second raw material of formula (V) and the catalyst is 1 to (1-5) to (0.05-0.5).

16. The preparation method according to claim 15, wherein a reaction temperature of the preparation process of the intermediate compound is 0-150° C., and a reaction time is 0.5-48 h.

* * * * *